US011142355B2

(12) United States Patent
Este et al.

(10) Patent No.: US 11,142,355 B2
(45) Date of Patent: Oct. 12, 2021

(54) MACHINE AND PROCESS FOR PREPARING INTRAVENOUS MEDICAMENTS

(71) Applicant: SWISSLOG ITALIA S.P.A., Milan (IT)

(72) Inventors: Flavio Este, Selvazzano Dentro (IT); Michele Minisini, Milan (IT)

( * ) Notice: Subject to any disclaimer, the term of this patent is extended or adjusted under 35 U.S.C. 154(b) by 80 days.

(21) Appl. No.: 16/082,660

(22) PCT Filed: Mar. 7, 2017

(86) PCT No.: PCT/IB2017/051316
§ 371 (c)(1),
(2) Date: Sep. 6, 2018

(87) PCT Pub. No.: WO2017/153905
PCT Pub. Date: Sep. 14, 2017

(65) Prior Publication Data

US 2019/0077526 A1 Mar. 14, 2019

(30) Foreign Application Priority Data

Mar. 7, 2016 (IT) ........................ 102016000023541

(51) Int. Cl.
*B65B 3/00* (2006.01)
*A61J 1/20* (2006.01)
(Continued)

(52) U.S. Cl.
CPC ................. *B65B 3/003* (2013.01); *A61J 1/20* (2013.01); *A61J 3/002* (2013.01); *G07F 17/0092* (2013.01); *B65B 3/04* (2013.01)

(58) Field of Classification Search
CPC .. B65B 3/003; B65B 3/04; A61J 3/002; A61J 1/20; G07F 17/0092; G07F 11/165
See application file for complete search history.

(56) References Cited

U.S. PATENT DOCUMENTS 5,309,959 A * 5/1994 Shaw ...................... B65B 3/003 141/103
5,341,854 A * 8/1994 Zezulka .................... A61J 1/20 141/1
(Continued)

FOREIGN PATENT DOCUMENTS

CN 102151228 A 8/2011
CN 203029630 U 7/2013
(Continued)

OTHER PUBLICATIONS

International Search Report issued in Application No. PCT/IB2017/051316 dated Aug. 8, 2017 (6 pages).
(Continued)

*Primary Examiner* — Timothy P. Kelly
(74) *Attorney, Agent, or Firm* — Flynn Thiel, P.C.

(57) ABSTRACT

A machine for preparing intravenous medicaments including an enclosing structure having a plurality of lateral walls arranged to define a closed internal working environment. An access station affords selective access to the closed internal working environment. One lateral wall is an equipped wall on which there are defined a plurality of stations for objects used in the preparation of intravenous medicaments. The stations on the equipped wall include temporary receiving or parking stations for the objects and operating stations for carrying out operations on the objects. A handling robot is programmed to transfer the objects from any station to any other station. The machine includes a metering module with one or more container support groups, a syringe support/metering member group, and a weighing group for weighing objects used in the preparation of intravenous medicaments.

34 Claims, 23 Drawing Sheets

(51) Int. Cl.

| | |
|---|---|
| ***A61J 3/00*** | (2006.01) |
| ***G07F 17/00*** | (2006.01) |
| *B65B 3/04* | (2006.01) |

(56) References Cited

U.S. PATENT DOCUMENTS

| | | | | |
|---|---|---|---|---|
| 5,431,201 | A * | 7/1995 | Torchia | A61J 1/20 141/100 |
| 6,006,946 | A | 12/1999 | Williams et al. | |
| 6,048,086 | A * | 4/2000 | Valerino, Sr. | B01F 13/1072 706/10 |
| 2011/0067781 | A1* | 3/2011 | Osborne | G07F 17/0092 141/37 |
| 2011/0208350 | A1 | 8/2011 | Eliuk et al. | |
| 2012/0048419 | A1* | 3/2012 | Giribona | B65B 3/003 141/1 |
| 2012/0241043 | A1* | 9/2012 | Perazzo | A61J 7/0053 141/2 |
| 2014/0202588 | A1 | 7/2014 | Aguerre et al. | |
| 2017/0128675 | A1* | 5/2017 | Koike | A61M 5/3291 |

FOREIGN PATENT DOCUMENTS

| | | | |
|---|---|---|---|
| WO | 9515142 | A1 | 6/1995 |
| WO | 2004014734 | A1 | 2/2004 |
| WO | 2009147252 | A1 | 12/2009 |

OTHER PUBLICATIONS

Written Opinion of International Searching Authority issued in Application No. PCT/IB2017/051316 dated Aug. 8, 2017 (11 pages).
Search Report and Written Opinion from the Intellectual Property Office of Singapore for corresponding Singapore Application No. 11201807603R, dated Nov. 8, 2019 (12 pages).

* cited by examiner

MACHINE AND PROCESS FOR PREPARING INTRAVENOUS MEDICAMENTS

FIELD OF THE INVENTION

The present invention relates to a machine and a process for preparing intravenous medicaments. The invention also relates to a metering module which is particularly suitable for use for preparing intravenous medicaments.

TECHNOLOGICAL BACKGROUND

There are known machines for preparing intravenous medicaments. The intravenous medicaments are prepared by mixing specific quantities of base products. In many cases, the resulting intravenous medicaments are stored in suitable containers, such as bottles, syringes, bags or elastomer materials and the like. The base products are contained in phials, bottles, bags and the like. During the preparation, a predetermined quantity of base product is removed from the relevant container. The removal of the base product from the relevant container is almost always carried out by means of a syringe.

In many hospitals, the preparation of intravenous medicaments is still carried out manually, even though machines for the automatic or semi-automatic preparation of those intravenous medicaments have become widespread and allow an improvement of the precision, an increase in productivity and ensure greater safety for the operators, especially in the case of handling toxic substances such as cytotoxic medical products and the like. The various containers used for the preparation of intravenous medicaments, such as bottles of base products, syringes for extraction of the base products and storage of the ready intravenous medicaments, bags, phials and the like, are introduced into machines of known type which provide for mixing of the base products so as to produce the required admixture of base products, in the correct doses and in the correct order.

The machines of known type are available in many forms and variants, which are not completely satisfactory. Some of them are bulky, others are expensive, or some machines provide a productivity level which is relatively low and difficult to scale in order to satisfy increased production requirements. Other machines are subject to potential errors during metering, while others are difficult to clean and sterilize. Still other machines do not ensure an adequate level of protection for the operators.

STATEMENT OF INVENTION

An object of the present invention is to provide a machine for preparing intravenous medicaments of an improved type with respect to the machines of known type. In particular, an object of the invention is to provide a machine which is safe, precise and relatively economical, but which can ensure good productivity. Furthermore, an object of the invention is to provide a machine whose productivity performance levels can be increased where applicable, without increasing the spatial requirement of the machine and at a fraction of the cost of the basic machine. Another object is to provide a machine which is simple to use, easy to clean, economical to use and to maintain, and safe for the operators. Another object of the invention is to provide a process which is particularly effective, rapid and safe for preparing an intravenous medicament by using a machine according to the invention.

Another object of the invention is to provide a metering module which is particularly effective for preparing intravenous medicaments to be used both per se, for example, in a state inserted in a laminar flow cabinet for use by an operator, and as a component of a more complex machine for preparing intravenous medicaments.

For the purpose of achieving the objects indicated above, the invention relates to a machine, a metering unit and a process for preparing intravenous medicaments having the features indicated in the appended claims.

According to a first aspect, a machine for preparing intravenous medicaments comprises an enclosing structure having a plurality of lateral walls which define the sides of a closed internal working environment. At least one access station is provided on at least one lateral wall of the enclosing structure for the selective access to the closed internal working environment, in which there are provided a plurality of stations for one or more objects which can be used in the preparation of intravenous medicaments. The plurality of stations comprise at least one temporary receiving or parking station which is provided for temporarily receiving one or more of the objects, and at least one operating station which is provided for carrying out operations on one or more of the objects for preparing intravenous medicaments. There is provided on at least one of the lateral walls, which thereby becomes an equipped wall, at least one temporary receiving or parking station and/or at least one operating station. The machine further comprises a handling robot which is arranged in the closed internal space of the machine. The handling robot is programmed to transfer the objects from any station which is selected from at least one access station, at least one temporary receiving station and at least one operating station, to any other of those stations.

Preferably, the handling robot is arranged in a substantially central position in the closed internal working environment. The handling robot comprises a handling hand and can rotate about a substantially vertical axis so as to be able substantially to reach with the handling hand any position on the lateral walls of the enclosing structure.

According to a particular aspect, the at least one equipped wall of the machine comprises:

at least one bottle parking station for bottles or the like, at least one ampoule parking station for ampoules or phials or the like, at least one syringe parking station for syringes or the like, at least one bag parking station for bags or the like.

According to a particular aspect, there is provided in a substantially central zone of the at least one equipped wall a preparation station which is suitable for using intravenous medicaments.

Preferably, bottle work supports are arranged around the preparation station.

Preferably, there is arranged below the preparation station a weighing device which is capable of weighing a bag and/or a bottle.

According to a particular aspect, the preparation station comprises a syringe support which can rotate about an axis which is substantially horizontal and movable in a substantially vertical direction, which support is provided with an engaging member for a syringe.

According to another particular aspect, the syringe support comprises a syringe actuator which is capable of selectively moving forwards or backwards the plunger of a syringe gripped by the engaging member so as to operate the syringe in a drawing or injecting manner.

There are preferably arranged on the at least one equipped wall one or more mixers which are capable of mixing the contents of one or more corresponding bottles.

The access station is preferably constructed in the form of a transit chamber which is constructed so as not to directly expose to the exterior the environment internal with respect to the machine.

Even more preferably, the transit chamber has two closure panels or doors, one directed towards the outer side of the enclosing structure so as to be accessible to an operator in order to introduce or withdraw contents to/from the transit chamber, and the other directed towards the internal working environment of the machine for removing or depositing contents by the handling robot.

According to another particular aspect, there can be inserted in the access station at least one tray which is provided with specific receiving members for the objects which are suitable for preparing the intravenous medicaments.

Preferably, the at least one tray comprises at least one receiving member which comprises a cavity with at least two mutually different internal diameters so as to be able to receive cylindrical objects with corresponding different basic diameters which substantially correspond to the different internal diameters of the cavity.

Even more preferably, the at least one tray further has at least one specific receiving member for syringes or the like.

According to another aspect, the machine is provided with a system for regulating the air inside the enclosing structure in order to maintain environmental conditions which are ideal for preparing the intravenous medicaments. The regulating system can place the interior of the machine at reduced pressure with respect to the external environment, thereby preventing discharges of powders or other products which are dangerous to the health of the operators. Alternatively, the regulating system can place the interior of the machine at excess pressure with respect to the external environment in order to prevent the introduction of contaminants into the machine.

Preferably, the internal working environment is maintained at a negative pressure in order to prevent the discharge of noxious or toxic products being processed therein.

According to another aspect, there is described a process for preparing intravenous medicaments by means of a machine of the above-indicated type, wherein there is provision for the following steps to be carried out asynchronously:

introduction of containers inside the machine;

removal of containers from the machine;

transfer of containers from a predetermined station to another predetermined station, which is carried out by the single handling robot;

subjecting the containers to operations for preparing intravenous medicaments which are carried out without the use of the handling robot.

Other characteristics and advantages will be appreciated from the following detailed description of a preferred embodiment, given by way of non-limiting example with reference to the drawings.

DETAILED DESCRIPTION

Figure 1:
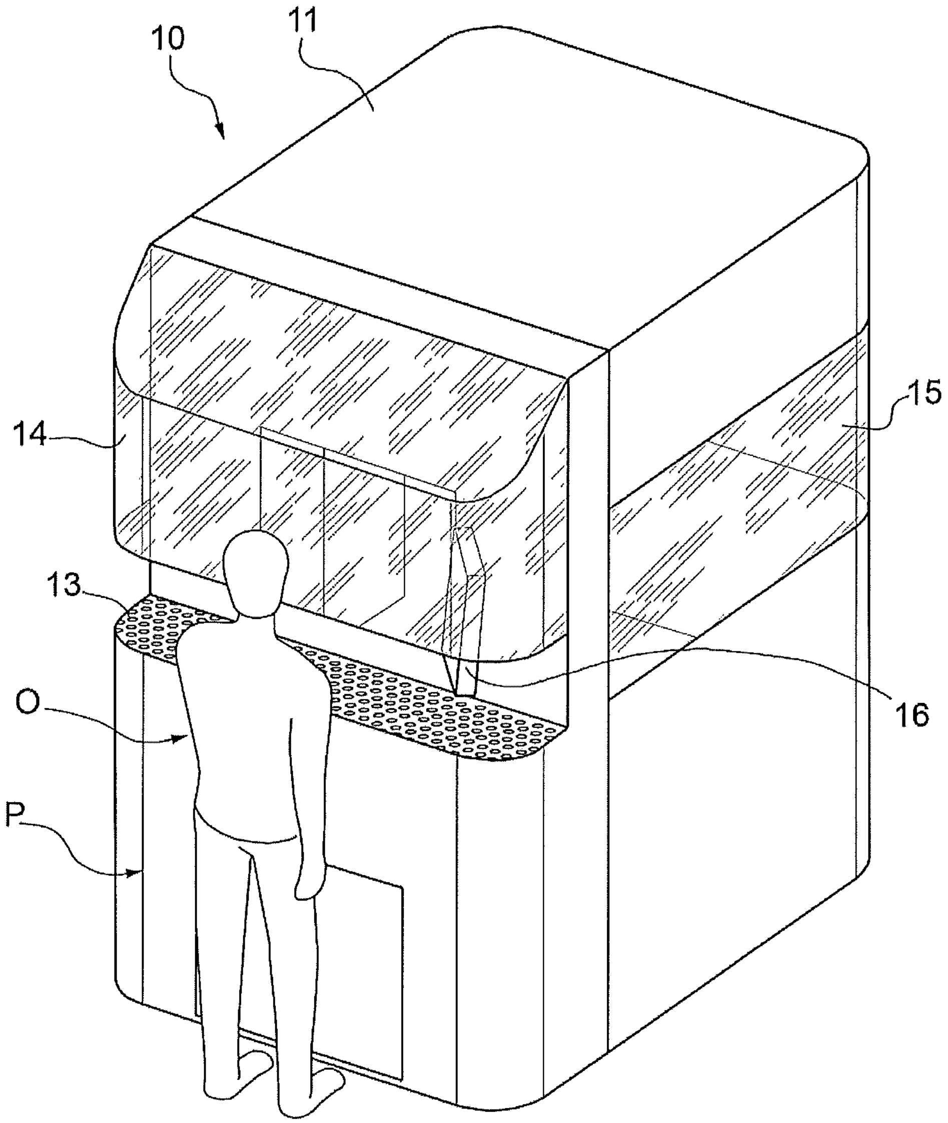
FIG. 1 is a perspective view from the exterior of a first version of a machine according to the invention.
Figure 2:
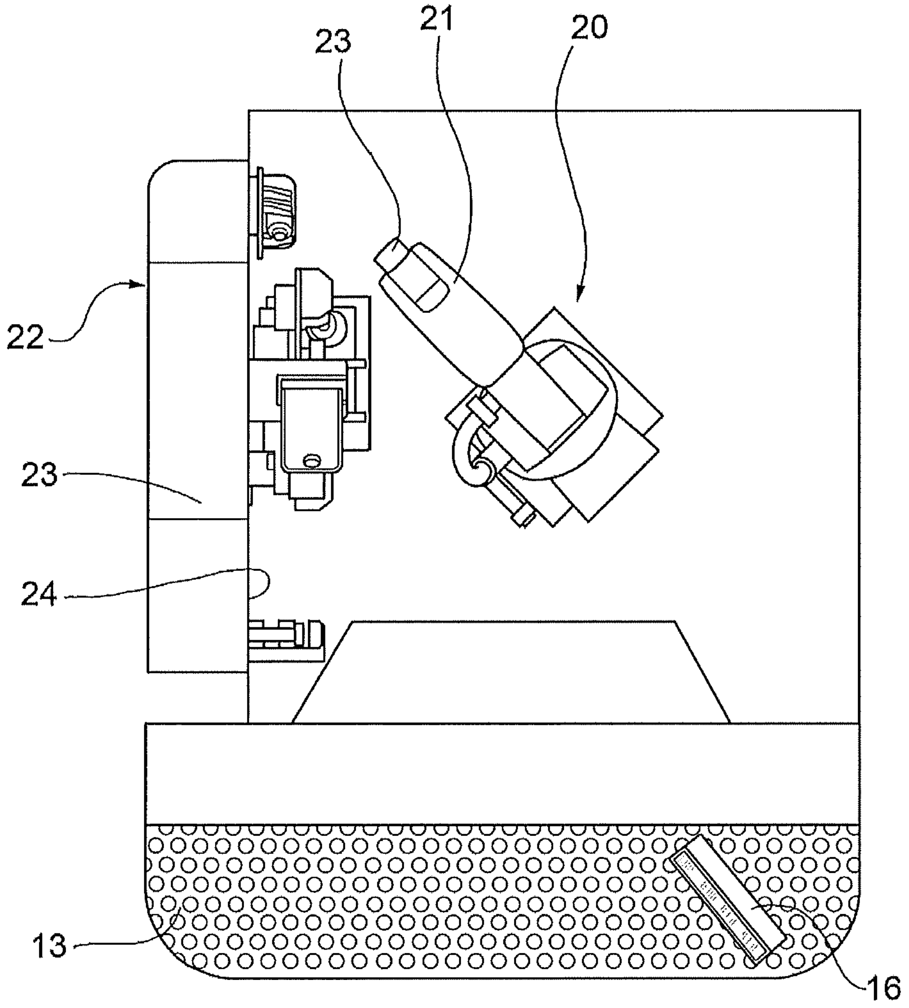
FIG. 2 is a plan view of the interior of the machine of FIG. 1.

With reference now to FIGS. 1 to 5, a machine 10 for preparing intravenous medicaments comprises an external enclosure 11 with an access 12 in the region of a work station P. The access 12 allows at least one operator O to introduce and withdraw products to/from a working environment which is defined inside the external enclosure 11. A support plane 13 is positioned in front of the access 12. A laminar flow cabinet 14 protects the access and covers the support plane 13. Preferably, the external enclosure 11 is provided with a transparent portion 15 for inspection of the interior of the machine 10. In the region of the work station P there is provided at least one data input and/or display device 16, such as a touch screen, a bar code reader or the like, or other known devices of the type. The access 12 is constructed in the form of a transit chamber which does not ever directly expose to the exterior the internal environment with respect to the machine. In particular, the transit chamber may have two closure panels or doors, one directed towards the outer side accessible to the operator in order to introduce or withdraw content to/from the transit chamber, and the other is directed towards the inner side of the machine and which can be opened automatically for removing or depositing content by the equipment of the machine, as will become clearer below. The two closure panels or doors of the transit chamber are controlled so as not to be both open at the same time: before allowing the opening of one of the two panels, the electronic control system of the machine establishes that the other panel is effectively closed.

Preferably, the machine 10 is provided with an air regulation system inside the enclosure 11, which system may comprise air recirculation, filtering of the air being drawn in and discharged and optional conditioning of the air. The regulation of the air inside the enclosure 11 allows ideal environmental conditions to be maintained for preparing the intravenous medicaments, at the same time avoiding discharges of powders or other products which are dangerous to the health of the operators, and minimizing the introduction of contaminants in the enclosure 11. Preferably, during operation, the interior of the machine 10 is maintained at a negative pressure in order to prevent the discharge of noxious or toxic products being processed therein. In a variant, the pressure inside the machine 10 is maintained at a positive pressure with respect to the external environment so as to prevent the introduction of contaminants inside the machine 10. In a variant, the machine is capable of modifying the individual internal pressure in such a manner that it can be alternatively in an excess pressure or reduced pressure state. It is preferable for the interior of the machine 10 to be maintained at reduced pressure when toxic active ingredients are being used, such as cytostatic agents, and therefore the discharge of any substances is considered to be a risk. Conversely, the machine can be operated at excess pressure for medicaments which are non-toxic, such as heparin, in which case the contamination by any external pathogens is considered to be a greater risk than a possible discharge of the active ingredient to the external environment.

Figure 5:
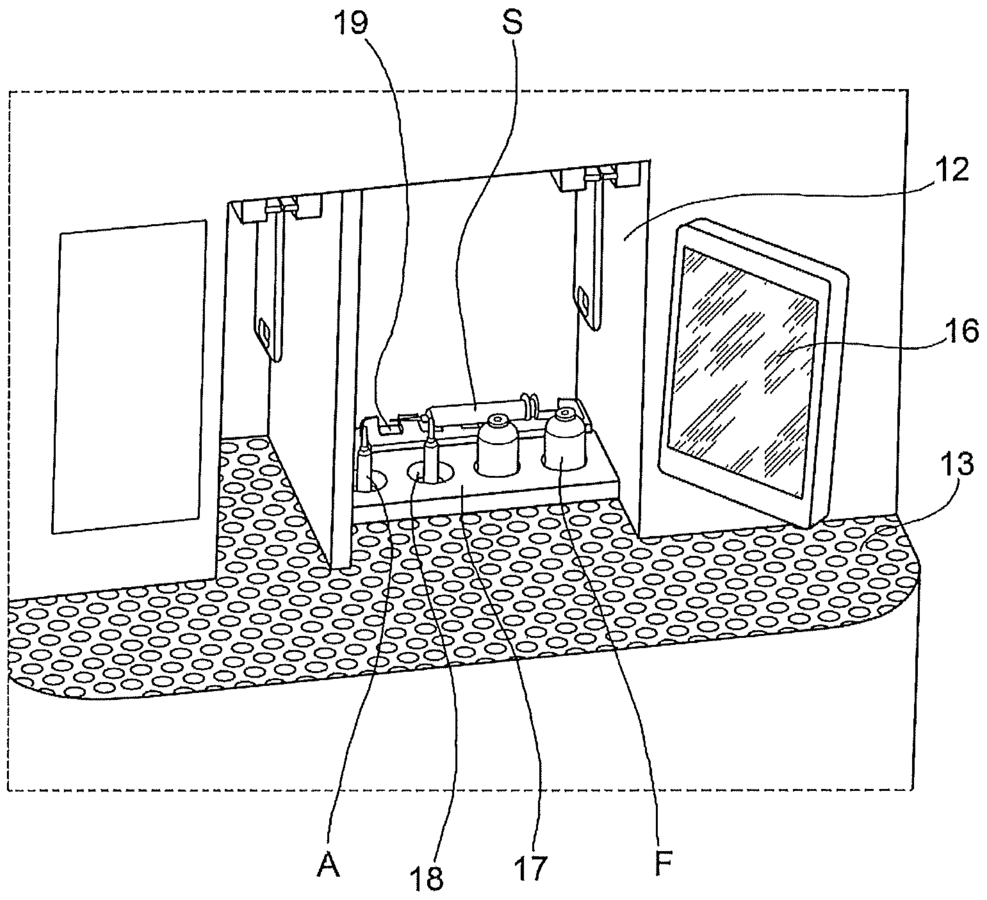
FIG. 5 is a perspective view, drawn to an enlarged scale, of the access opening of the machine of FIG. 1.

With reference to FIG. 5, the access 12 particularly allows introduction inside and withdrawal from the machine 10 of one or more trays 17 which are provided with specific receiving members 18 for objects which are suitable for preparing the intravenous medicaments, including bottles F or the like, ampoules A or the like. In particular, the receiving members 18 for bottles F and ampoules A are each constructed to have a cavity in the tray 17 having two different diameters so as to produce a step so as to be able to receive both cylindrical bottles F having a base diameter substantially corresponding to the greater diameter of the cavity of the receiving member 18 and thinner ampoules A having a smaller diameter substantially corresponding to the smaller diameter of the cavity of the receiving member 18. Naturally, this solution is not limited to the arrangement of only two different diameters of the receiving members 18, but instead may be generalized by producing steps with a plurality of mutually different diameters so as to be able to adapt to as many different diameters of bottles F and/or ampoules A and/or other receiving members. The trays 17 also have specific receiving members 19 for syringes S or the like, which are used during the preparation of the intravenous medicaments. FIG. 5 shows by way of non-limiting example a tray 17 which has four aligned receiving members 18 and a receiving member 19 for a syringe S. The predetermined number of objects which can be arranged on the tray 17 makes it simple to handle the products to be used and it is not necessary to have vision systems for recognizing what has been introduced into the machine 10 via the tray 17 by the operator O.

Inside the external enclosure 11, in a substantially central position in the working environment, there is provided a handling robot 20. The handling robot 20 can rotate about a vertical axis and has articulated arms 21 which terminate in a handling hand 23 which can reach any position on the walls which delimit the working environment, in particular in order to move the bottles F, the ampoules A, the syringes S and one or more bags B for collecting the intravenous medicaments, as will become clearer below.

The example of FIGS. 1 to 5 illustrates a first embodiment of the machine 10, in which the internal working environment comprises an equipped side 22 which groups together the machinery which is provided for preparing the intravenous medicaments. The equipped side 22 comprises a box-like structure 23, in which specific movement mechanisms and the electronic actuation system are arranged. The box-like structure 23 has an equipped internal wall 24, from which the pieces of equipment of the machinery provided for preparing the intravenous medicaments project.

Figure 3:
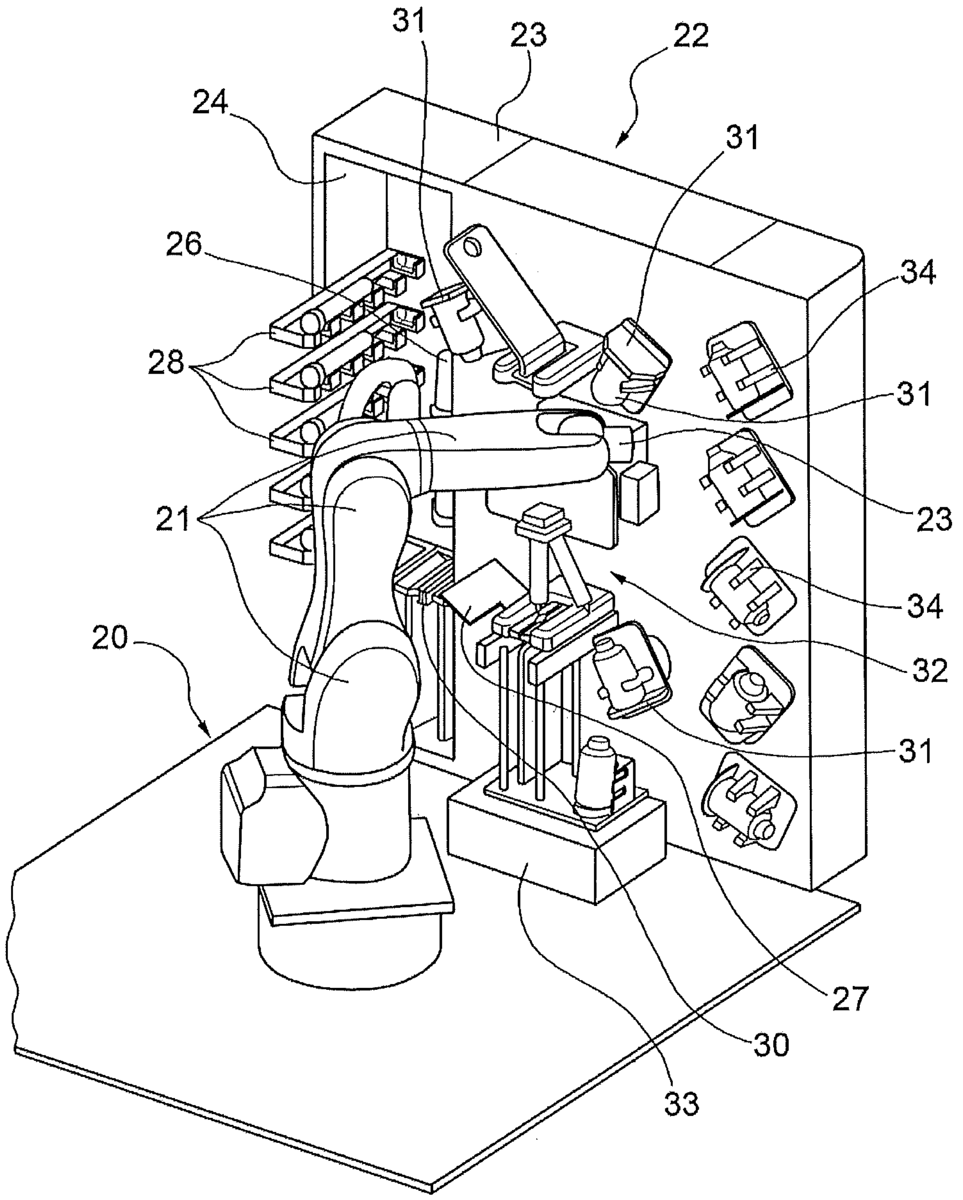
FIG. 3 is a perspective view of the internal mechanisms of the machine of FIG. 1, including a preparation group and a handling robot.
Figure 4:
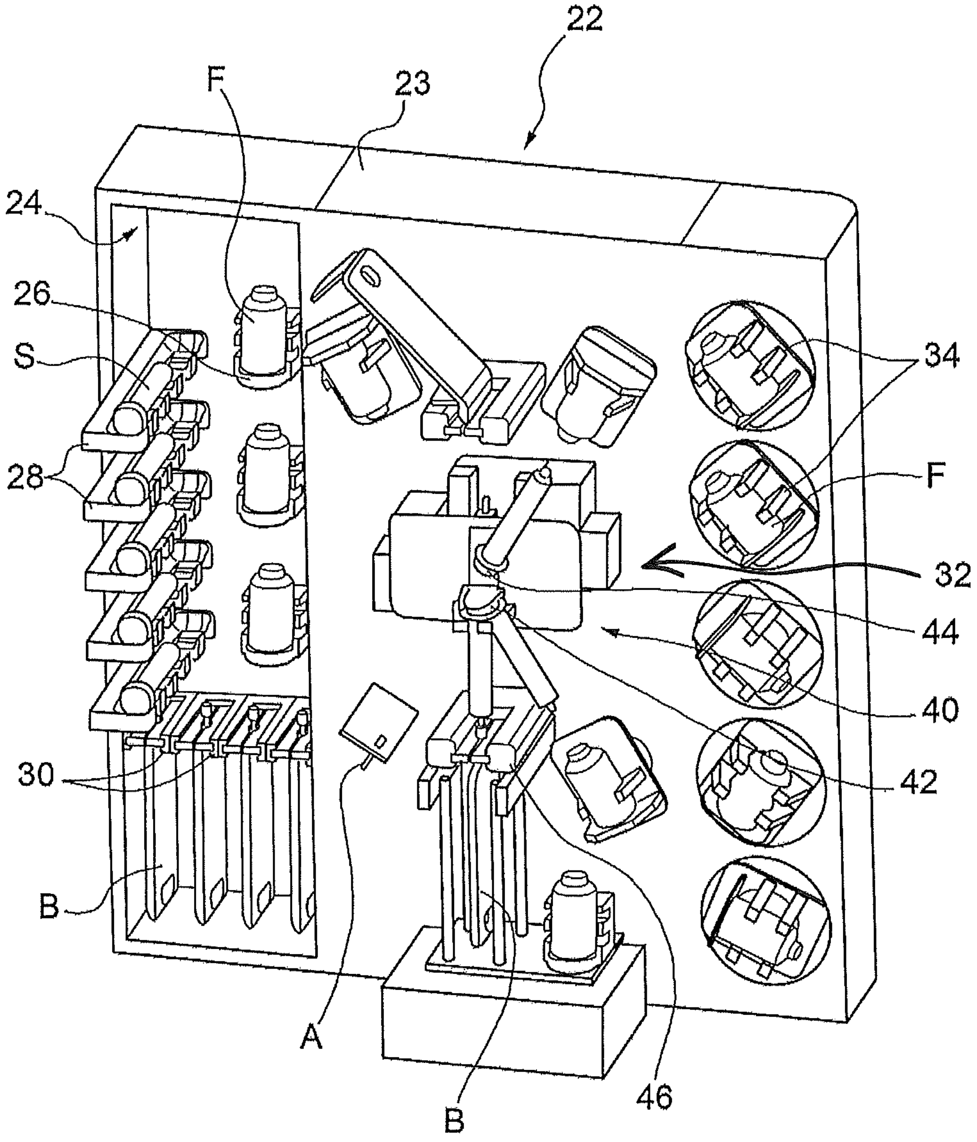
FIG. 4 is a perspective view of the single preparation group of the machine of FIG. 1.

As can better be seen in FIGS. 3 and 4, the equipped wall 24 comprises at least one bottle parking station 26 for bottles F or the like. The equipped wall 24 comprises at least one ampoule parking station 27 for ampoules or phials A or the like. The equipped wall 24 comprises at least one syringe parking station 28 for syringes S or the like. The equipped wall 24 comprises at least one bag parking station 30 for bags B or the like.

In a substantially central zone of the equipped wall 24 there is arranged a preparation station 32 which is suitable for using intravenous medicaments, as will be described more clearly below. Bottle work supports 31 are arranged around the preparation station 32. There is positioned below the preparation station 32 a weighing device 33 which is capable of weighing a bag B and/or a bottle F. There are provided on the equipped face 24 mixers 34 which are capable of mixing the contents of the bottles F. In the embodiment illustrated in FIGS. 3 and 4, by way of example which must not be considered to limit the present invention, the equipped wall 22 comprises three bottle parking stations 26, five syringe parking stations 28, four bag parking stations 30, five mixing members 34 and three bottle work supports 31 which are arranged around the single preparation station 32.

As can better be seen in FIG. 4, the preparation station 32 comprises a syringe support 40 which is rotatable about a horizontal axis and which is movable in a vertical direction, and which is provided with an engaging member 42 which is preferably a pair of pincers which is capable of selectively gripping the body of a syringe S. The syringe support 40 also comprises a syringe actuator 44 which is capable of selectively moving the plunger of a syringe S gripped by the engaging member 42 forwards or backwards so as to operate the syringe S so as to draw in or inject. The movement of the syringe support 40 in rotation and in a vertical direction allows a syringe S which is held by the engaging member 42 to be moved away from and towards the opening of a bag B which is arranged on a bag work support 46, or away from and towards the opening of a bottle F which is retained on one of the bottle work supports 31.

The ampoule A, after being loaded on the machine, is transported into the working area or into the storage area. The device 27 provides for keeping the ampoule A gripped so as to allow the robot, by means of the pair of pincers with which it is provided, to break the upper nozzle of the ampoule A. After the ampoule A has been opened in this manner, the contents thereof can be readily drawn in by means of a syringe.

Figure 6:
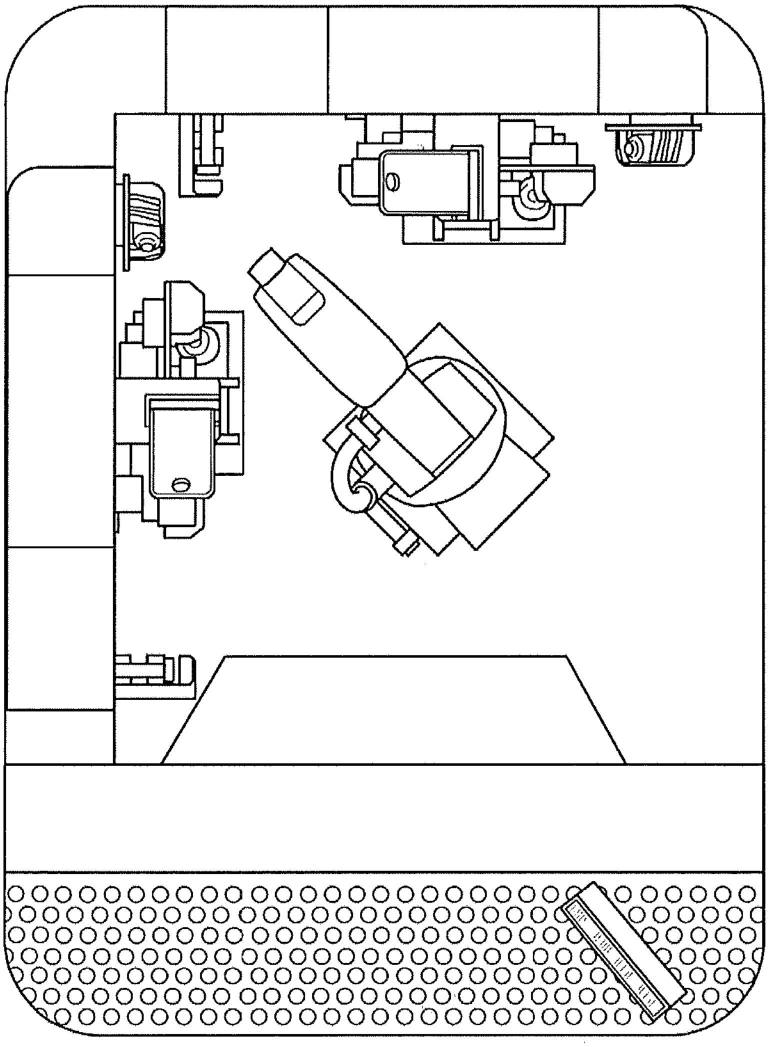
FIG. 6 is a plan view, similar to FIG. 2, of the interior of a second version of a machine according to the invention.
Figure 7:
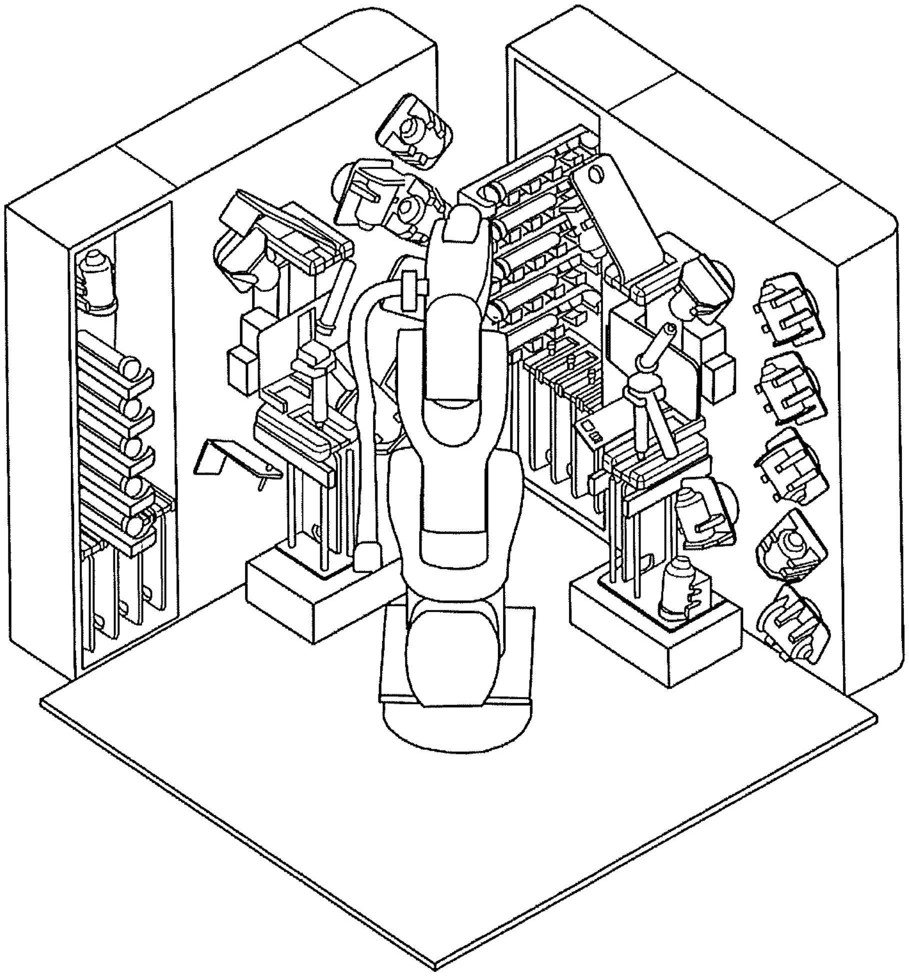
FIG. 7 is a perspective view of the internal mechanisms of the machine of FIG. 6, including two preparation groups and a common handling robot.
Figure 8:
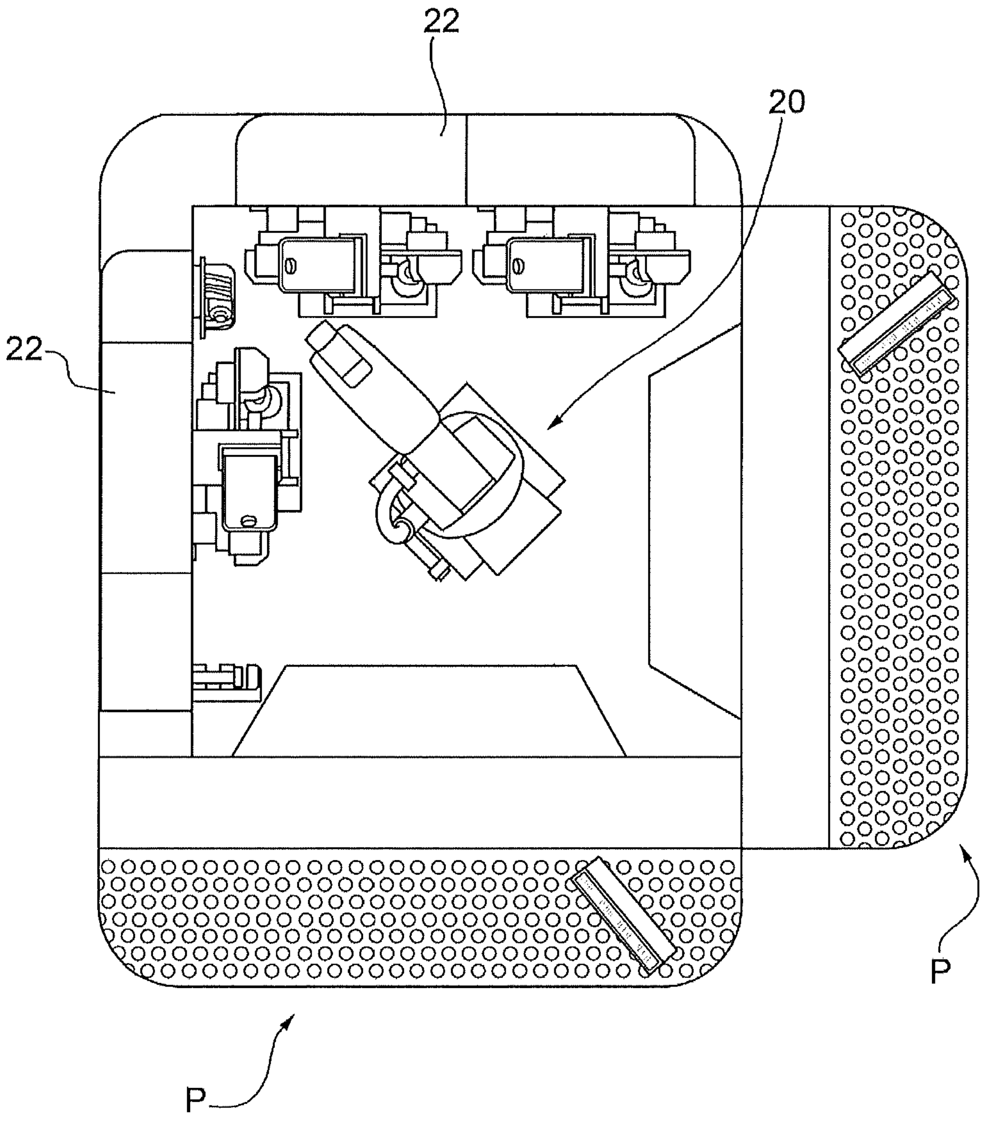
FIG. 8 is a plan view, similar to FIGS. 2 and 6, of the interior of a third version of a machine according to the invention.

FIGS. 6 and 7 illustrate a variant of the machine 10, which is provided with two equipped sides 22 of the type described above, which are served by a single handling robot 20 which is arranged at the centre of the machine 10. This version allows the productivity of the machine 10 to be doubled with costs and dimensions which are substantially less than double those of the entire machine. The machine may provide for a single work station P, as illustrated in FIG. 1, or may be modified with the provision of a second work station P on another side of the machine so as to operationally use all four sides of the machine, two for operator stations P, two for equipped sides 22, as can be seen in FIG. 8. Naturally, it is also possible to configure the machine 10 with a single work station P and three equipped sides 22. The plan geometry of the machine 10 is not further limited to the quadrilateral form, it being possible to construct a machine 10 with five or more sides, of which some are used operationally by equipped sides 22 and others by work stations for operators. Those variants have in common the modularity of the equipped sides 22 and the work stations P which are identical to each other and which can be increased in number in order to correspondingly increase the productivity of the machine 10, with costs and dimensions which are reduced as a result of the use of a single handling robot 20.

For preparing intravenous medicaments, an operator O present in the work station P is dedicated to introducing into the machine 10 through the access 12 desired products. The process for preparing intravenous medicaments may be carried out in accordance with various methods, depending on how the basic components are arranged and how it is desired to supply the finished product. The most common operations provide for the charging of bottles or bags, which may contain active ingredients or diluents, and the discharge, that is to say, the supply of the intravenous medicament ready for use, in bottles, bags or syringes. There will be described below some operations which can be carried out by means of the machine of the present invention without the number or the sequence of operations indicated being limiting for the processes which can be carried out with programming of the machine in accordance with specific requirements. In fact, as a person skilled in the art may understand from a reading of the present description, the machine of the present invention is particularly flexible and the operations which the machine may carry out are of various types and are not limited to the ones which have been described here.

In particular, the operator O positions one or more bottles F and/or ampoules A on a tray 17 which is arranged in the transit chamber of the access 12 to the opening of the external door thereof. The identification of the products positioned on the tray 17 is carried out by the operator, for example, with input of the identification data of the products in the administration system of the machine 10 via the data input device 16. After the tray 17 has been positioned inside the transit chamber of the opening 12, the external door is closed and the opening of the internal door is authorized so that the handling robot 20 inside the machine 10 can reach the products placed on the tray 17. The handling robot 20 then provides for a transfer of the bottles F and/or ampoules A from the tray 17 to respective bottle parking stations 26 or ampoule parking stations 27. The handling robot 20 also provides for the transfer of the optional syringe S which is positioned on the tray 17 to a respective syringe positioning station 28. Preferably, the bottles F are weighed on the balance 33 before being transferred to the respective bottle parking positions 26. In this case, the handling robot 20 provides, preferably during the weighing of each bottle F, for the removal of other objects from the tray 17 or in any case for other transfer operations of other objects in accordance with methods which will be discussed below. After the bottle F has been weighed, the handling robot 20 provides for the transfer thereof from the balance 33 to a parking position 26, or, if the processing station 32 is ready for use, directly on one of the bottle work supports 31.

The operator may also introduce into the opening 12 one or more bags B which, once introduced into the machine 10, are removed by the handling robot 20 and transferred to a corresponding bag parking position 30. It should be noted that the handling robot 20 is occupied with these operations only for the time necessary for transferring the objects. Furthermore, the transfer of the objects to the respective parking positions does not necessarily have to be carried out when the products are introduced into the machine 10, but may instead be postponed, even in a differentiated manner for each product present on a single tray 17, in accordance with the working cycles in progress inside the machine 10, in accordance with an optimized and asynchronous control logic with respect to the preparation operations for the intravenous medicaments, which will be explained herein below.

The actual preparation of the intravenous medicaments is carried out by means of operations carried out by the preparation station 32. In this regard, one of the syringes S is taken from the parking position 28 by the handling robot 20 and carried to the syringe support 40 of the preparation station 32, where the engaging member 42 grips it. The handling robot 20 further provides for a bottle F to be taken from the parking position 26 thereof and to be transferred to one of the bottle work supports 31. One of the bags B is also taken from the parking position 30 thereof and carried to the operating position, on the bag work support 46 positioned below the syringe support 40.

The ampoules A are stored on a parking support which is provided in the area 24. The ampoules A can be transported from that support towards the system 27 where an automatic position holding system is provided. The robot, by means of a movement of the pair of pincers with which it is provided, brings about the breakage of the nozzle of the ampoule A, which is thereby ready for the contents thereof to be drawn out by a syringe. The broken nozzle is transported by the robot towards the discharge.

When a syringe is placed and retained in the preparation station 32, the syringe support 40 is orientated and moved in such a manner that the needle of the syringe can be introduced into the stopper of a bottle F in order to remove therefrom dilution liquid to be transferred to an ampoule, or to inject therein, for example, an active ingredient to be diluted.

Once the product to be diluted has been injected in one of the bottles F positioned on one of the bottle operating supports 31, the handling robot 20 provides for the bottle F to be taken in order to transfer it to one of the mixers 34, which is directed in order to mix the contents of the bottle F. In accordance with the specific configuration of the mixer 34, the mixer can be activated so as to rotate continuously at a predetermined number of revolutions, or with alternating rotation in two directions, or in an oscillating manner, at constant or unequal speeds, in accordance with the profile settings for mixing which may also be specific in accordance with the product to be mixed.

At the end of the mixing operation, the bottle F can be transferred again to a bottle operating support 31 in order to remove therefrom the contents to be injected into a bag B, or it may be moved to a bottle parking position 26, or it may be transported towards the opening 12. All those movements are carried out by the handling robot 20, which is also used for other movements of objects, such as, for example, the transfer of a syringe S from the syringe support 40 in order to transfer it into a disposal zone (not illustrated in the Figures), for example, into a container for hospital waste which is positioned inside the machine 10 and which is periodically emptied by an operator.

It should be noted how, in all the cases mentioned above, the handling robot 20 is used for the time strictly necessary for transferring the objects from one station to another. The handling robot 20 is released immediately after the transfer of an object, without having to wait for the time necessary for the various steps for preparing the intravenous medicaments.

With reference now to FIGS. 9 to 23, there is described in detail a metering module 100 which can be used to form one of the internal walls of the machine described above. The metering module 100 can also be used alone, for example, by providing it inside a laminar flow cabinet so as to be able to be used by an operator without using the handling robot 20 described above.

Figure 9:
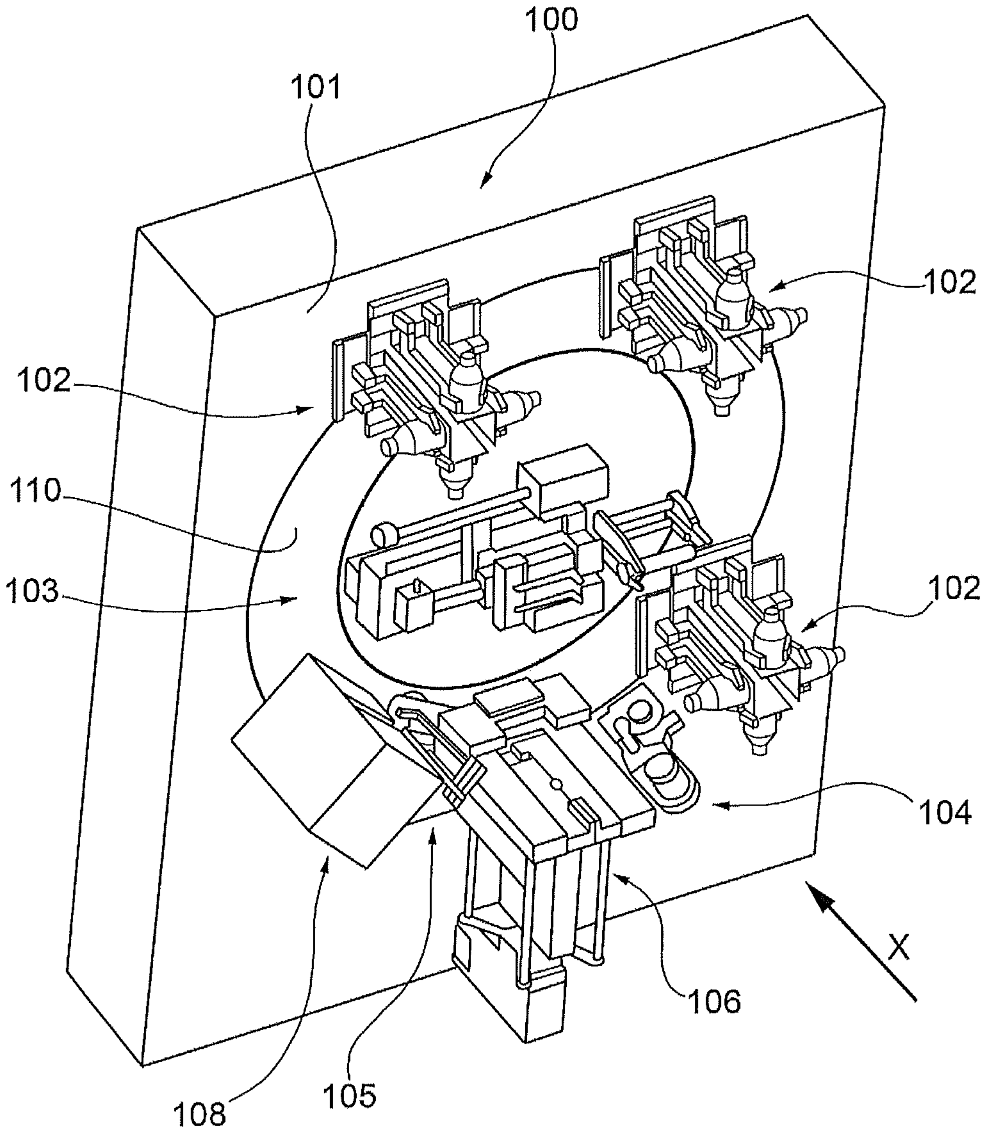
FIG. 9 is a perspective view of a metering module.
Figure 10:
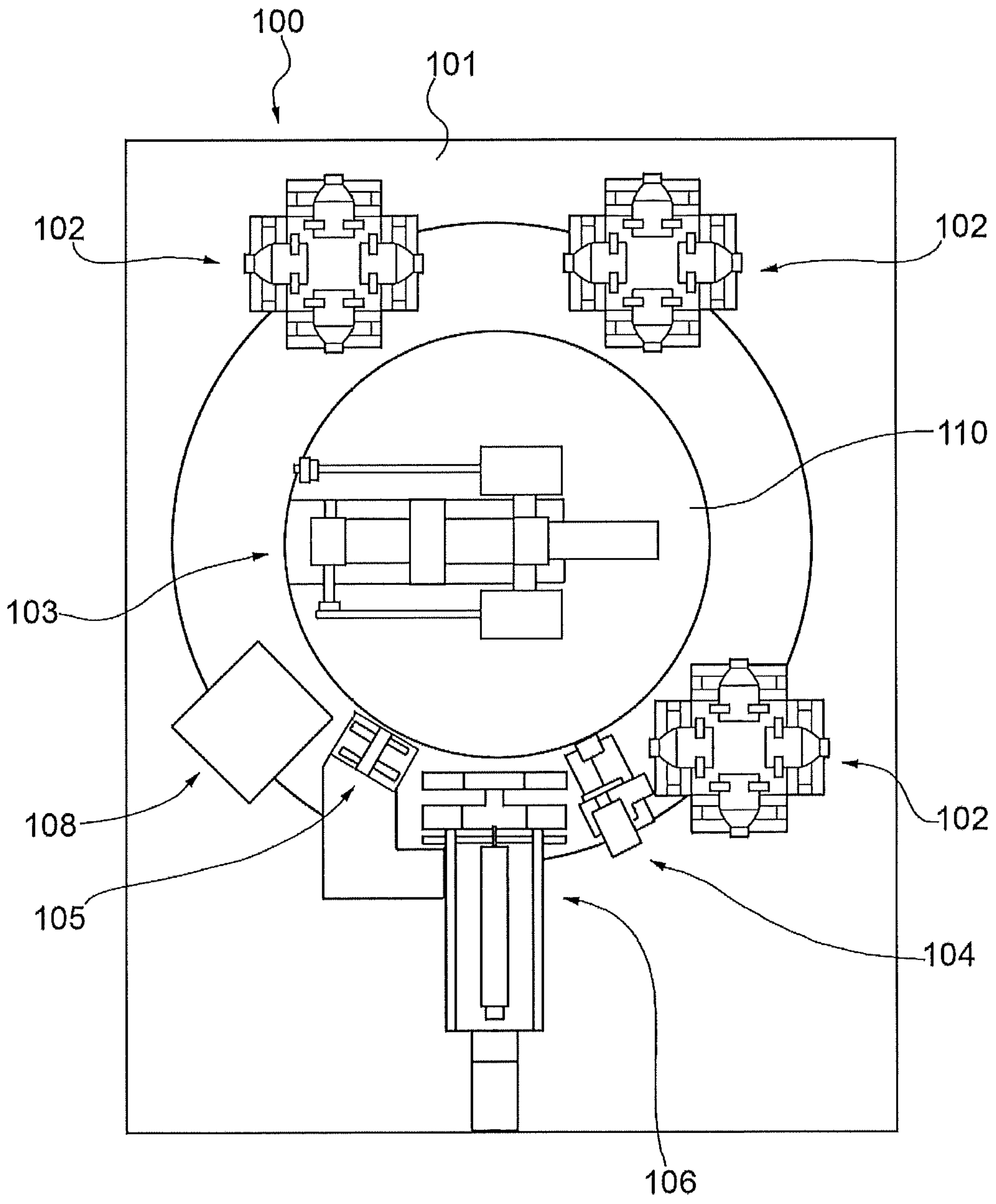
FIG. 10 is a front view of the metering module in accordance with the arrow X of FIG. 9.

With reference to FIGS. 9 and 10, a metering module 100 comprises an equipped wall 101 which contains the movement members and the electronics for actuating different groups which protrude therefrom. The metering module 100 comprises one or more container support groups 102. The metering module 100 preferably comprises a syringe support/metering member group 103, and the use of a plurality of syringe support/metering member groups 103 is not excluded. The metering module comprises a needle unscrewing and/or syringe plugging group 104, and the use of a plurality of needle unscrewing and/or syringe plugging groups 104 is not excluded. The metering module comprises a syringe weighing group 105, and the use of a plurality of syringe weighing groups 105 is not excluded. The metering module comprises a bag weighing group 106, and the use of a plurality of bag weighing groups 106 is not excluded. There can also be mounted on the equipped wall a washing station 108 for the needles and the pairs of needle-holding pincers of the metering support.

In the embodiment illustrated in FIGS. 9 and 10, the metering module 100 comprises a single syringe support/metering member group 103 which is arranged on the equipped wall 101 in a substantially central position. Some container support groups 102 (three in the example of the Figures), a needle unscrewing and/or syringe plugging group 104, a syringe weighing group 105 and—in a lower position—a bag weighing group 106 are arranged around the syringe support/metering member group in a substantially radial arrangement.

The syringe support/metering member group is mounted on a rotary platform 134 which is actuated by a motor group 132 which allows it to rotate in the vertical plane of the equipped wall 101 so as to turn from time to time towards the various groups which radially surround it, as will become clearer from the following detailed description. The main characteristic of the metering module 100 is that all the operations on the objects stored thereon can also be carried out without the intervention of a handling robot or an external operator. In this sense, the metering module 100 constitutes an autonomous operating unit.

Figure 11:
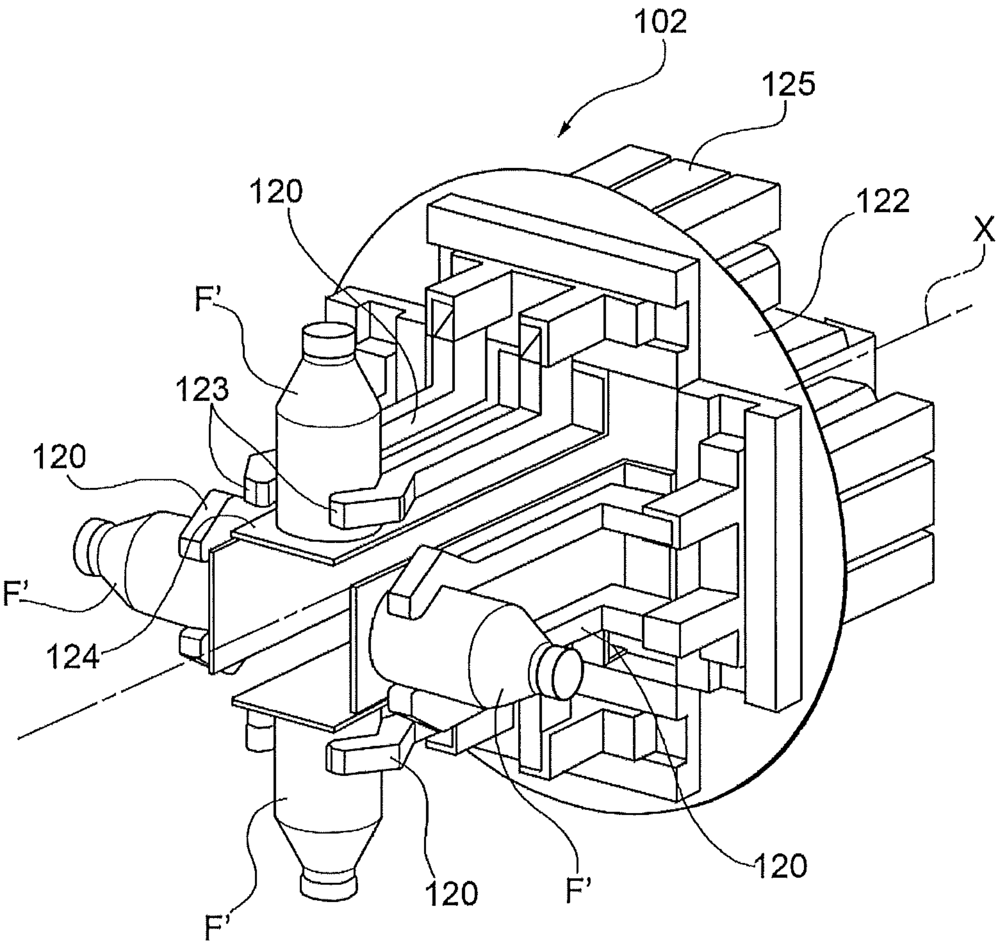
FIG. 11 is a perspective view of a container support group of the metering module of FIGS. 9 and 10.
Figure 12:
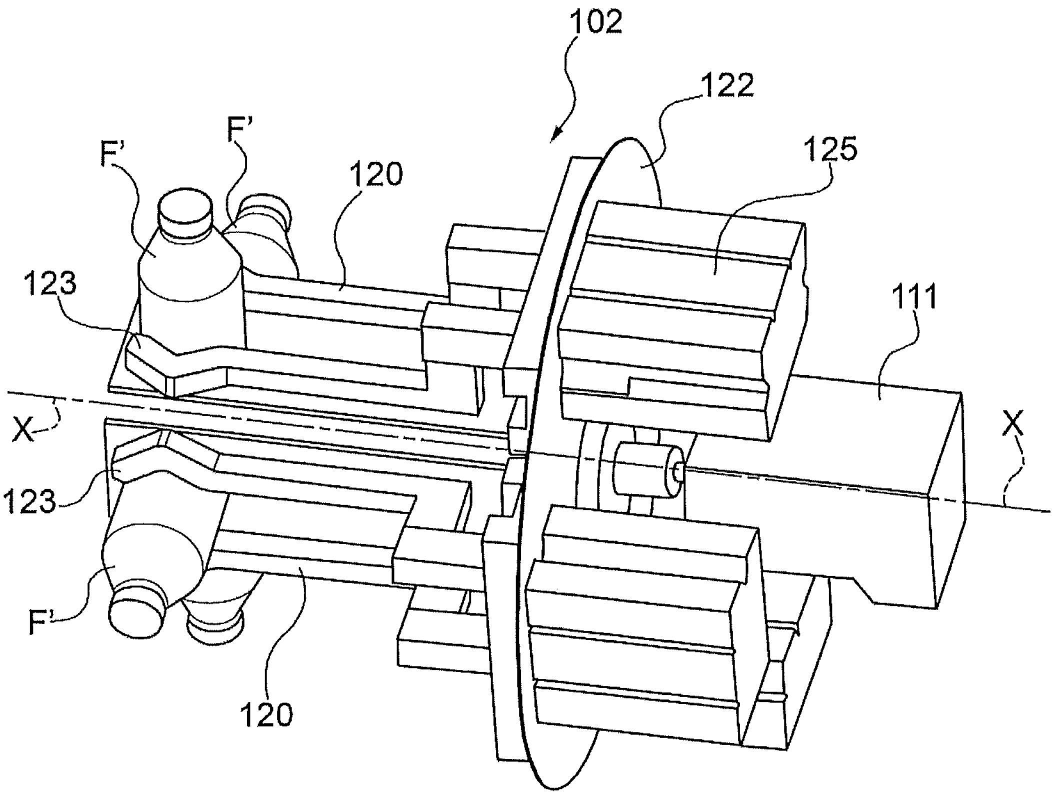
FIG. 12 is a view according to a different perspective of the container support group of FIG. 11.
Figure 13:
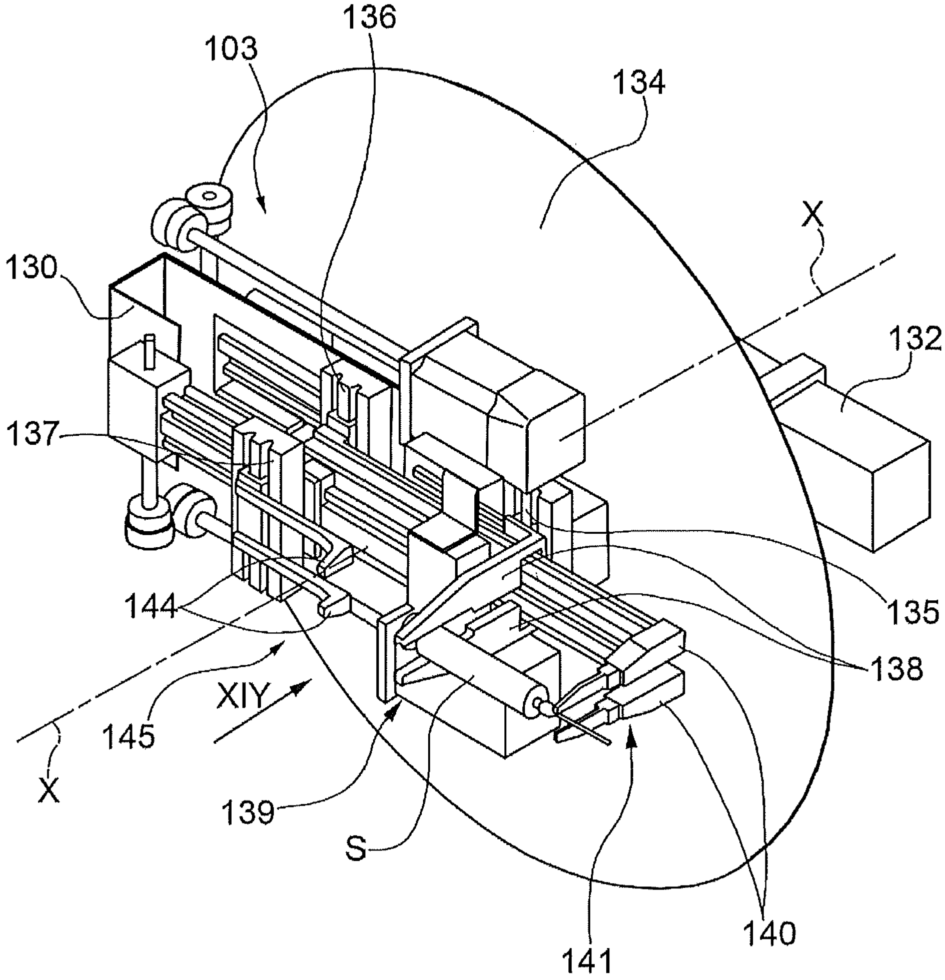
FIG. 13 is a perspective view of a syringe support group/metering member of the metering module.
Figure 14:
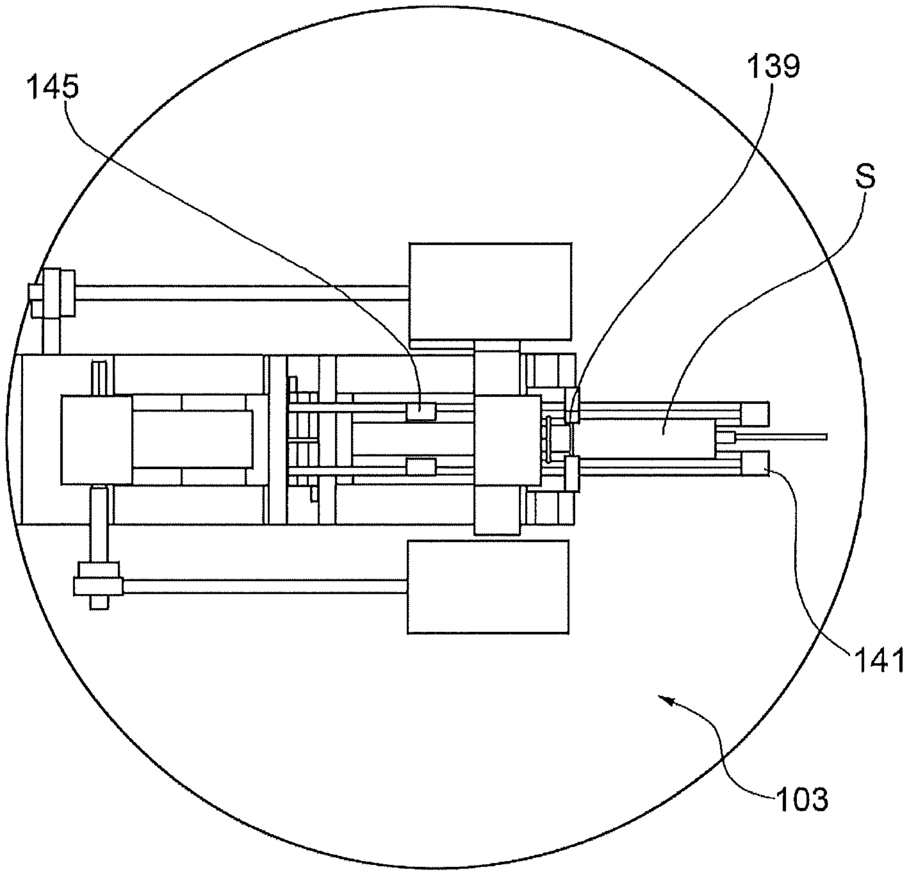
FIG. 14 is a front view of the syringe support group/metering member in accordance with the arrow XIV of FIG. 13.
Figure 15:
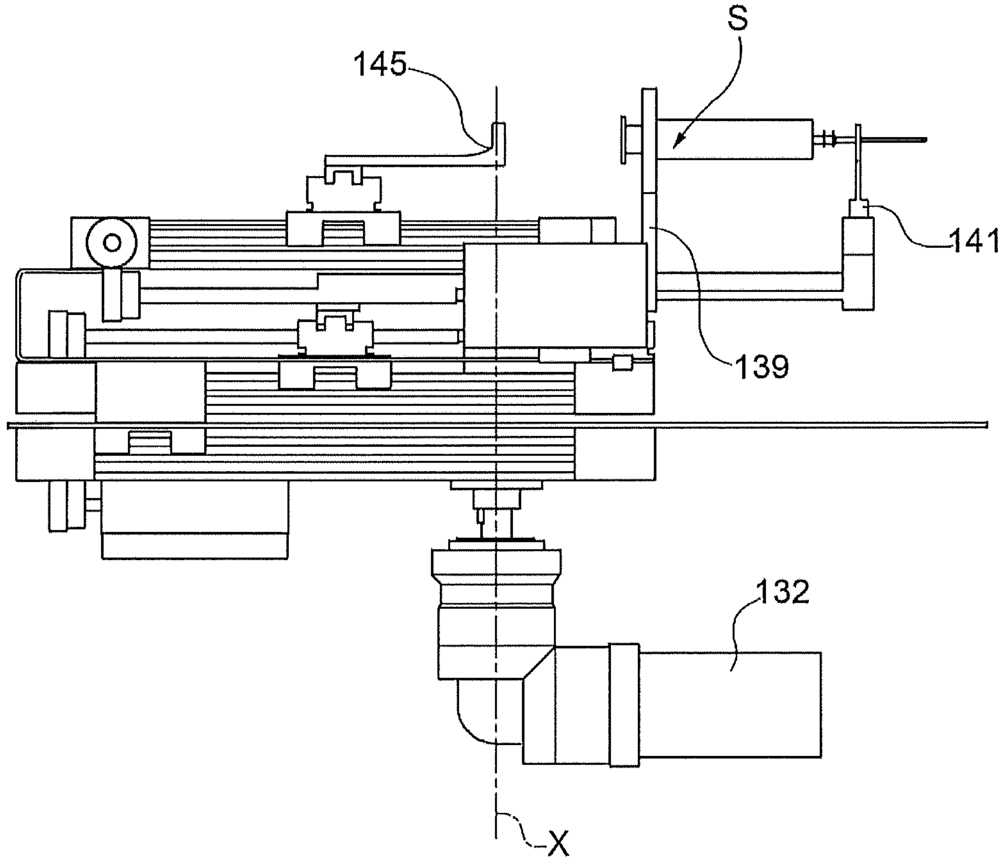
FIG. 15 is a cross-sectional view of the syringe support group/metering member of FIGS. 13 and 14.
Figure 16:
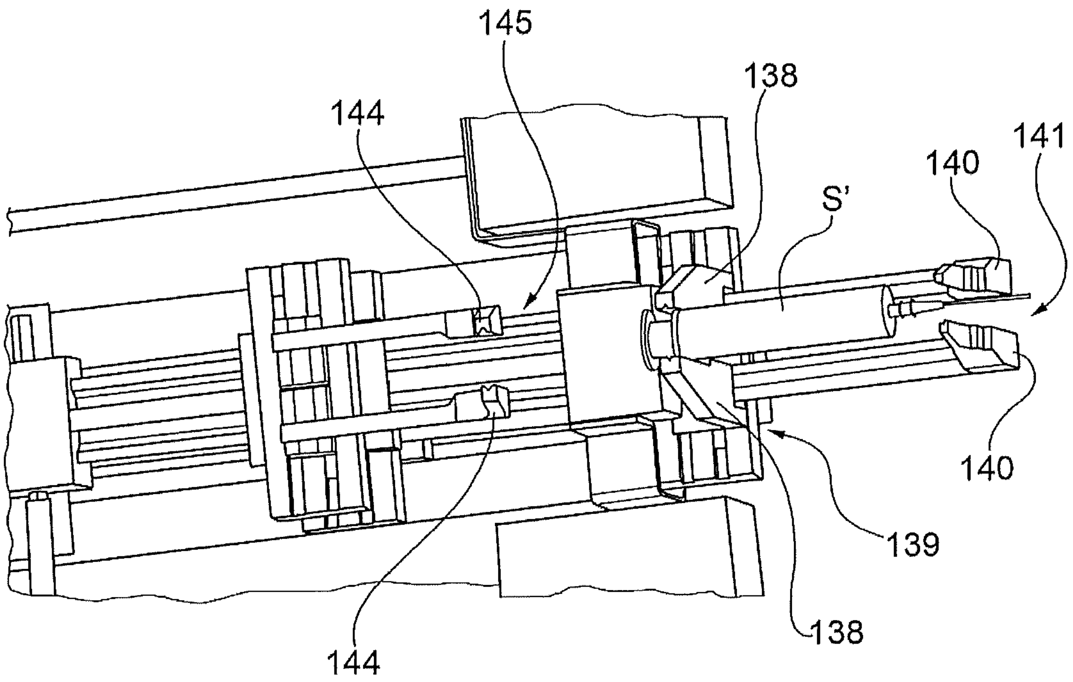
FIG. 16 is a view from above of the syringe support group/metering member of FIGS. 13, 14 and 15.

With reference now to FIGS. 11 and 12, the container support group 102 serves to retain closed containers F' to be used with the metering system. The containers F' may contain both liquids and powders and can therefore be used both for drawing in a substance from the interior thereof and for injecting a substance at the inner side thereof. One and/or other of those two substance extraction or injection functions can be repeated several times on the same container F', independently of the positioning of the container F' on the container support group 102 and the installation location of the module with respect to the metering unit. The containers F' are generally closed containers which can contain a liquid or powder and can be both rigid (for example, bottles, small bottles, ampoules) and flexible (for example, bags, elastomeric pumps), which are formed by a plurality of materials (for example, glass+plastics material, different plastics materials) or by a single material (for example, glass or plastics material).

The container support group 102 comprises a series of pairs of pincers 120 which project from the equipped wall 101. The pairs of pincers 120 are arranged around a substantially horizontal axis X-X of a rotary member 122. Preferably, each container support group 102 comprises four pairs of pincers 120 which are arranged at 90°. Each pair of pincers 120 comprises two jaws 123 which are capable of gripping a container F'. There is arranged under all the jaws 123 a support plate 124 for the container F'. The jaws 123 are actuated by an actuator mechanism 125. Each container support group 102 can therefore support a plurality of containers F' at the same time. As a result of the rotary member 122, the container support group 102 can rotate by means of the motor group 111 in order to position a container F' beside the syringe support/metering member group 103. The pairs of pincers 120 can work autonomously and in any position to allow them to be charged with a container F' while at the same time another pair of pincers 120 is used in the metering zone.

It is possible to use the container support group 102 in such a manner that the containers F' which can no longer be used are allowed to fall simply by opening the respective pairs of pincers 120. To this end, there is provided below the container support group a basket or the like for collecting the containers F' which are allowed to fall from the container support group 102. The container support group 102 is autonomous per se and can be constructed so as to be able to be disengaged from the equipped wall 101 so as to be carried en bloc towards a new position. For example, the container support group 102 could be disengaged and carried towards a separate charging position so as to charge the entire system externally with respect to the metering module 100. In a variant, the pairs of pincers 120 can be autonomously disengaged from the container support group 102 so as to be carried independently to a charging position, leaving the motor member of the container support group 102 in position on the equipped wall 101.

Various positions of the container support group 102 which are defined by different rotation angles about the axis X-X can be associated with different functionalities. For example, it is possible to have a container charging position, a container discharge position, an injection and/or drawing-in position, a weighing position, a disinfection position, a bar code and/or label reading position and a container opening position (for example, if the container is an ampoule).

With reference now to FIGS. 13 to 16, the syringe support/metering member group 103 serves to support syringes S or the like in order to carry out the metering operations. In particular, it serves to retain and use the syringes S and the like and to transport them towards various positions inside the metering module 100 where various functions are carried out, such as liquids being drawn in or injected, weighing, washing, identification and evaluation of the weight and/or other characteristics, for example, by means of vision systems such as tele-cameras and the like, the closure of the metering objects, connection and/or disconnection of needles or other external systems (for example, bags, elastomeric pumps, connection tubes, etc.), and in general all the functions which can be carried out on the objects for metering such as the syringes S or the like.

The syringe support/metering member group 103 comprises a base support 130 which can rotate about an axis X-X and which is connected to a main rotation motor 132 which is arranged behind a circular plate 134 which defines a portion of the plane of the equipped wall 101. In this manner, the main rotation motor 132 remains arranged inside the equipped wall 101 while the base support 130 projects outside it. All the base support 130 may optionally move in translation along a transverse axis with respect to the axis X-X as a result of a transverse movement system.

There is mounted on the base support a linear syringe body runner 135, a linear syringe needle runner 136 and a linear syringe plunger clamping runner 137, each one being capable of sliding on a respective linear guide and being controlled by a transmission operated by a relevant motor.

There are mounted in a movable manner on the linear syringe body runner 135 two jaws 138 of a pair of syringe body clamping pincers 139. The two jaws 138 can be opened and closed about the body of a syringe S or the like, preferably being brought into abutment with the wings of the syringe S opposite the receiving member of the needle.

There are mounted in a movable manner on the linear syringe needle runner 136 two jaws 140 of a pair of syringe needle clamping pincers 141. The two jaws 140 can be opened and closed about the needle support of the syringe S in order to insert it or remove it. The pair of syringe needle clamping pincers 141 is capable of controlling both syringes S with clamping of the needle of the Luer Lock type and other types of clamping, for example, "Luer Slip Tip", "Eccentric Luer Slip Tip", "Catheter Tip" and in general all the connections between syringes and needles based on press-fitting in addition to models with screw type fitting, such as the ones provided with a Luer Lock system and the like. The pair of syringe needle clamping pincers 141 can carry out centring of the needle with the injection and/or drawing tip by means of an autonomous movement with respect to the rest of the metering system. The pair of syringe needle clamping pincers 141 can keep the needle in contact with the syringe S in order to allow the use of types of connection with pressure between the needle/syringe. As a result of the linear runner 136, the pair of syringe needle clamping pincers 141 can allow the needle to be removed from the syringe S by means of a longitudinal movement with respect to the axis of the syringe. The pair of syringe needle clamping pincers 141 can also carry out the removal of the needle covering cap. The pair of syringe needle clamping pincers 141 can be completely withdrawn in order to allow the body of the syringe to be completely free and therefore to afford the possibility of manipulating the syringe in other sub-units, such as, for example, weighing the syringe without it being necessary for the robot arm to intervene, or to temporarily park the syringe inside the system. The pair of pincers 141 can be extended beyond the limit of the needle in order to be able to be washed inside the washing unit 108 so as to prevent any problems of cross-contamination of the medicaments.

There are mounted in a movable manner on the linear syringe plunger clamping runner 137 two jaws 144 of a pair of syringe plunger clamping pincers 145. The two jaws 144 can be opened and closed about the rod of a syringe plunger S in order to extract it from and insert it in the syringe S in order to operate in accordance with drawing in and injection.

The syringe support/metering member group 103 is capable of being moved in rotation about the axis X-X as a result of the motor 132. The syringe S can further carry out translation movements in accordance with an axis perpendicular to the axis X-X mainly as a result of the capacity for linear movement of the pair of syringe body clamping pincers 139 which is mounted on the linear runner 134. It is thereby possible to operate on any points over the periphery of the syringe support/metering member group 103 without any need for provision of predetermined mechanical blocks or stops.

The characteristics of the syringe support/metering member group 103 allow the use of syringes S having different dimensions without, however, being limited to a single format or single mark. The settings in relation to the various syringes S are saved inside a database of the electronic processing system and afford the capacity for modifying the operating configuration when changing the syringe and/or needle.

It is possible to configure the syringe support/metering member group 103 so as to allow the syringe to fall after it has been used. To that end, it is possible to provide a basket or the like below the syringe support/metering member group 103. This prevents the use of the handling robot for unloading the syringe which can thereby be carried out automatically.

Figure 17:
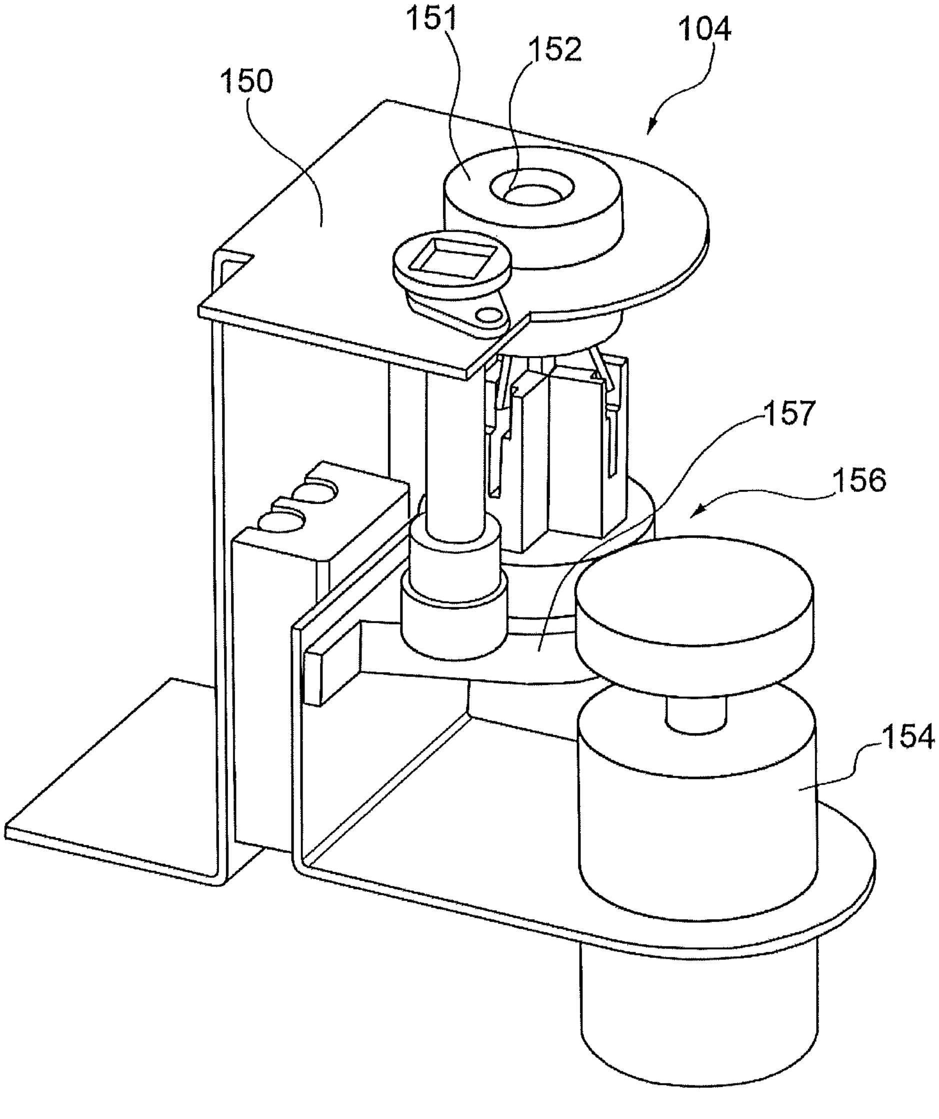
FIG. 17 is a perspective view of a needle unscrewing and/or syringe plugging group of the metering module.
Figure 18:
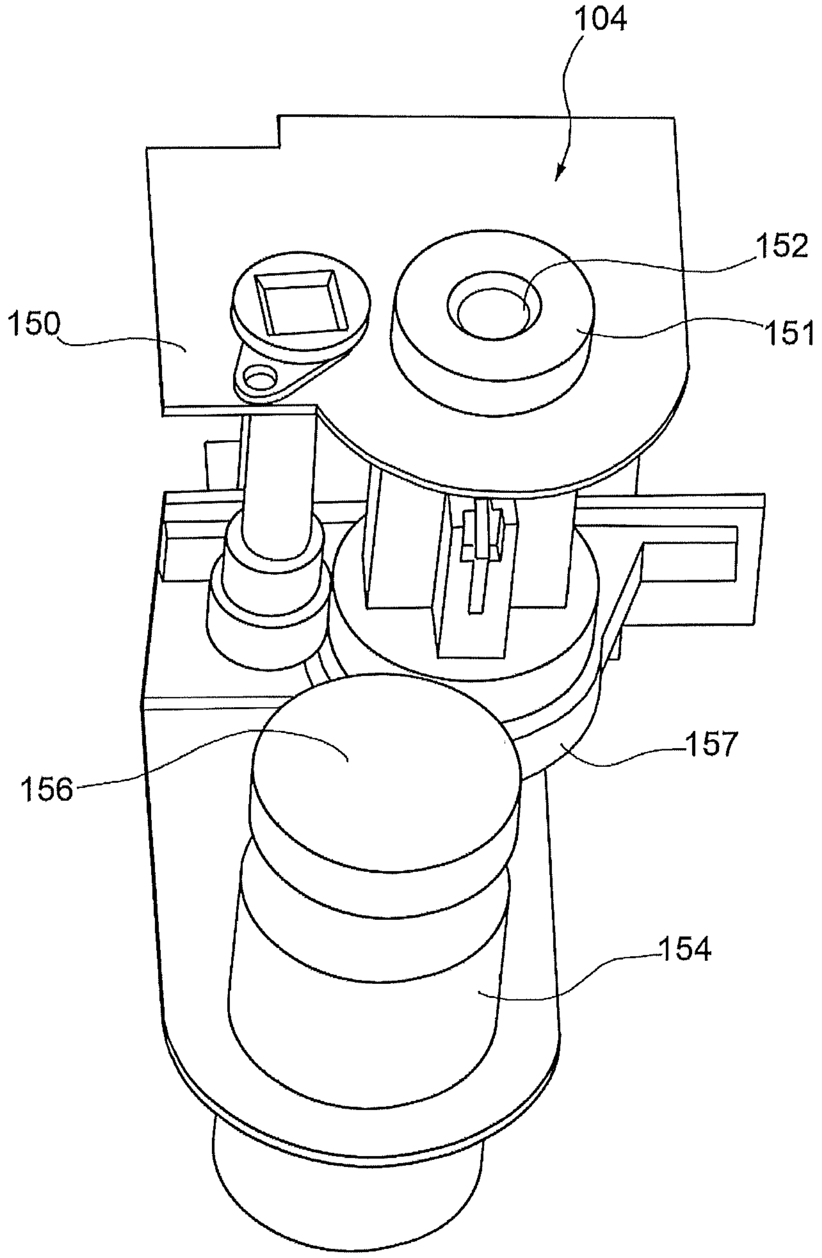
FIG. 18 is a view according to a different perspective of the needle unscrewing and/or syringe plugging group of FIG. 17.
Figure 19:
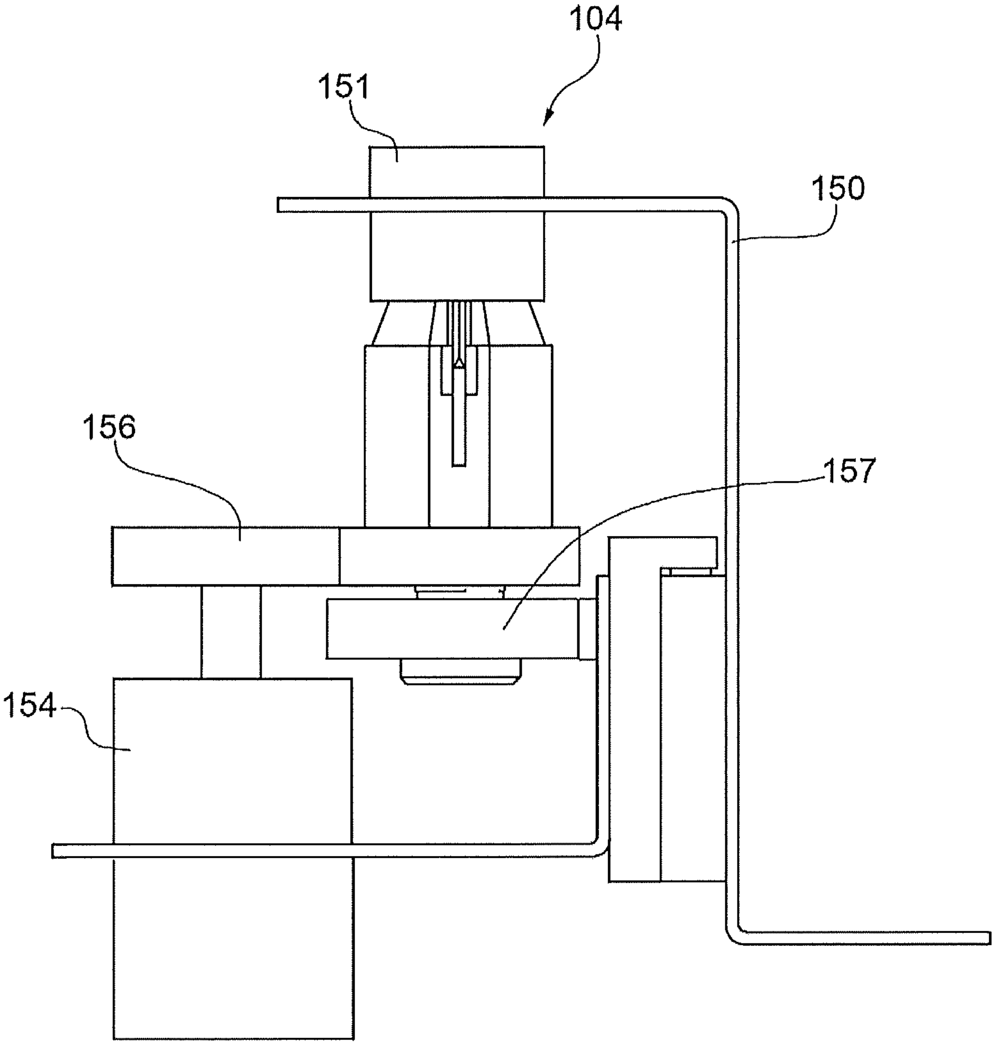
FIG. 19 is an elevation view of the needle unscrewing and/or syringe plugging group of FIGS. 17 and 18, FIGS. 20 and 21 are two views in accordance with different perspectives of a syringe weighing group of the metering module.

With reference now to FIGS. 17 to 19, a needle unscrewing and/or syringe plugging group 104 allows rotation and/or retention of objects such as needles or covers for syringes. This group comprises a main member 150 on which there is mounted an operating member 151 which has a receiving member 152 for receiving and gripping a member, for example, a syringe needle or a syringe cover. A motor 154 is connected with a transmission 156 to the operating member 151 so as to rotate it selectively with control. There is associated with the operating member 151 a translation member 157, for example, a plunger, for pressing the cover on the syringe S or withdrawing the needle from the syringe S.

The group 104 is capable of unscrewing the needles connected with or without a Luer Lock system. The group 104 is capable of covering the syringes with covers both under pressure and in a screwable manner. All the materials retained by the group 104 can be caused to fall automatically, for example, into a basket or the like underneath, so as not to require the intervention of the robot arm.

Figure 20:
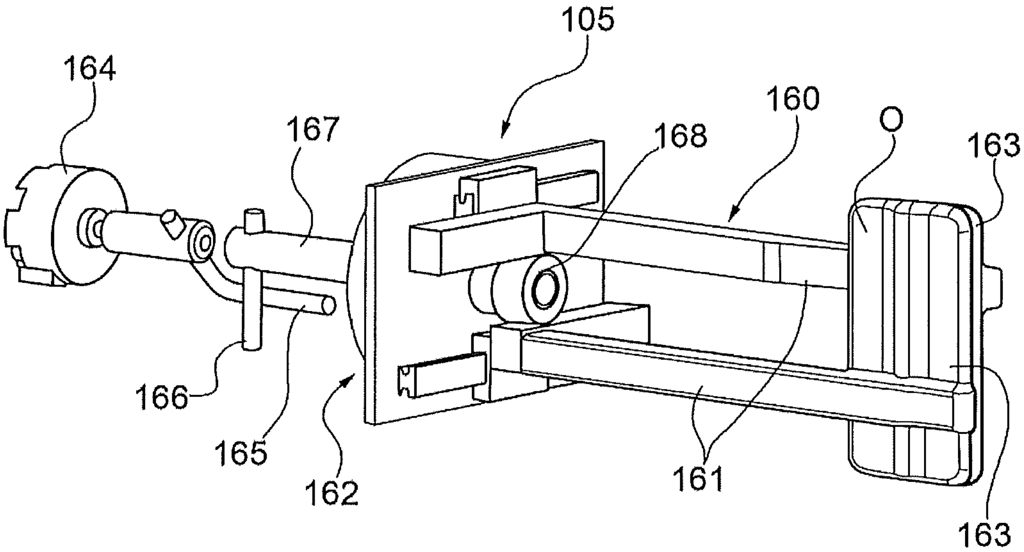
Figure 21:
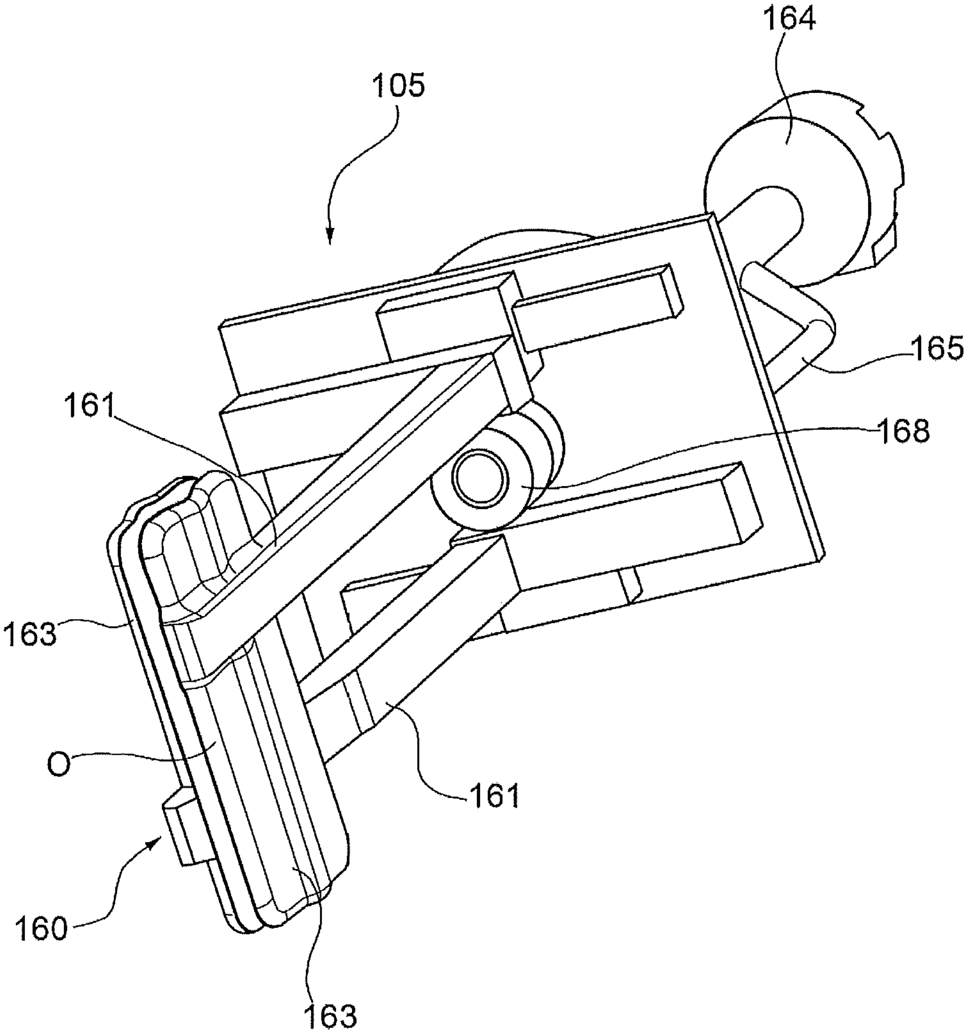

With reference now to FIGS. 20 and 21, the syringe weighing group 105 comprises an engaging element 160. The engaging element 160 preferably comprises two arms 161 which are capable of gripping a syringe S or other object to be weighed by retaining it between two jaws 163 so that it is secured only to a balance 162. The two arms 161 are loaded by a spring which urges each of them in the direction of the other. A motor 164 is connected to an eccentric arm 165 which acts only at one side of a radial peg 166 which is fixed to a shaft 167 provided with a transmission 168 which by rotating moves the arms 161 away by acting counter to the action of the spring. When the syringe weighing group 105 is in a waiting position, the motor 164 urges the eccentric arm 165 against the radial peg 166 in such a manner that the arms 161 remain remote from each other by acting counter to the action of the spring. In order to weigh an object O, for example, a syringe, the object O is arranged between the arms 161, the motor 164 is actuated so as to move the eccentric arm 165 away from the radial peg 166 and therefore to obtain mechanical isolation between the balance 162 and the motor 164, so as not to affect the measurement.

Naturally, the system for isolating the syringe weighing group 105 can also be constructed differently from the one illustrated. The group 105 is in any case used in order to retain the syringe or another object, such as bags, bottles, ampoules, needles, covers and elastomer bags, allowing them to be weighed without the intervention of the robot arm or an external operator. As indicated in the specific example of the Figures, the automatic closure system of the engaging element 160 can be actuated by a spring which stores energy as a result of the closure thereof, while the opening is carried out by means of a motor or external rotation which loads the spring and keeps the engaging element 160 open. The motor could be of the electrical type, supplied by a battery and controlled in a wireless manner. The motor could be of the electrical type, supplied and controlled by means of an electrical field nearby. An alternative actuation system could use the accumulation of a pressurized fluid.

Figure 22:
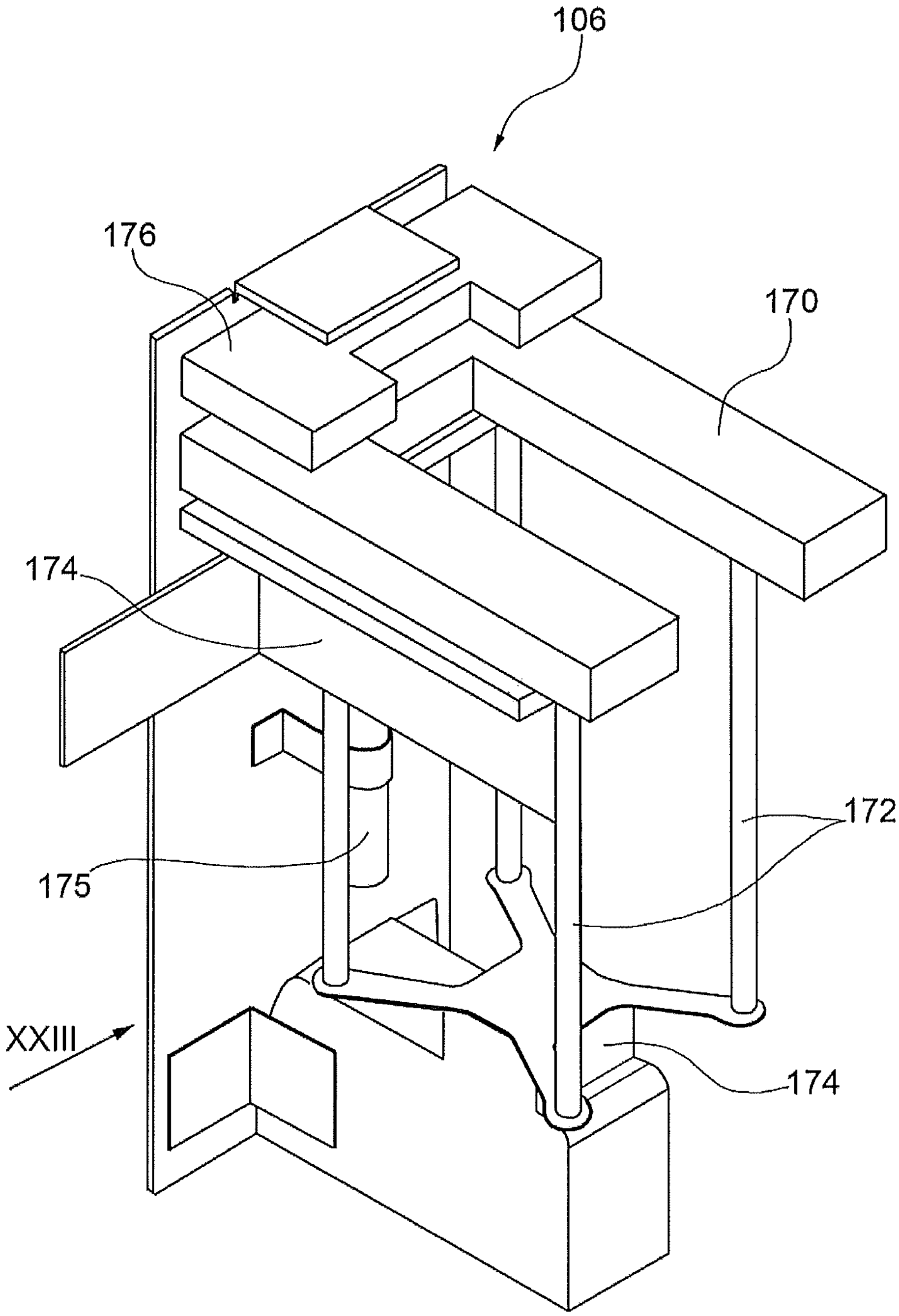
FIG. 22 is a perspective view of a bag weighing group.
Figure 23:
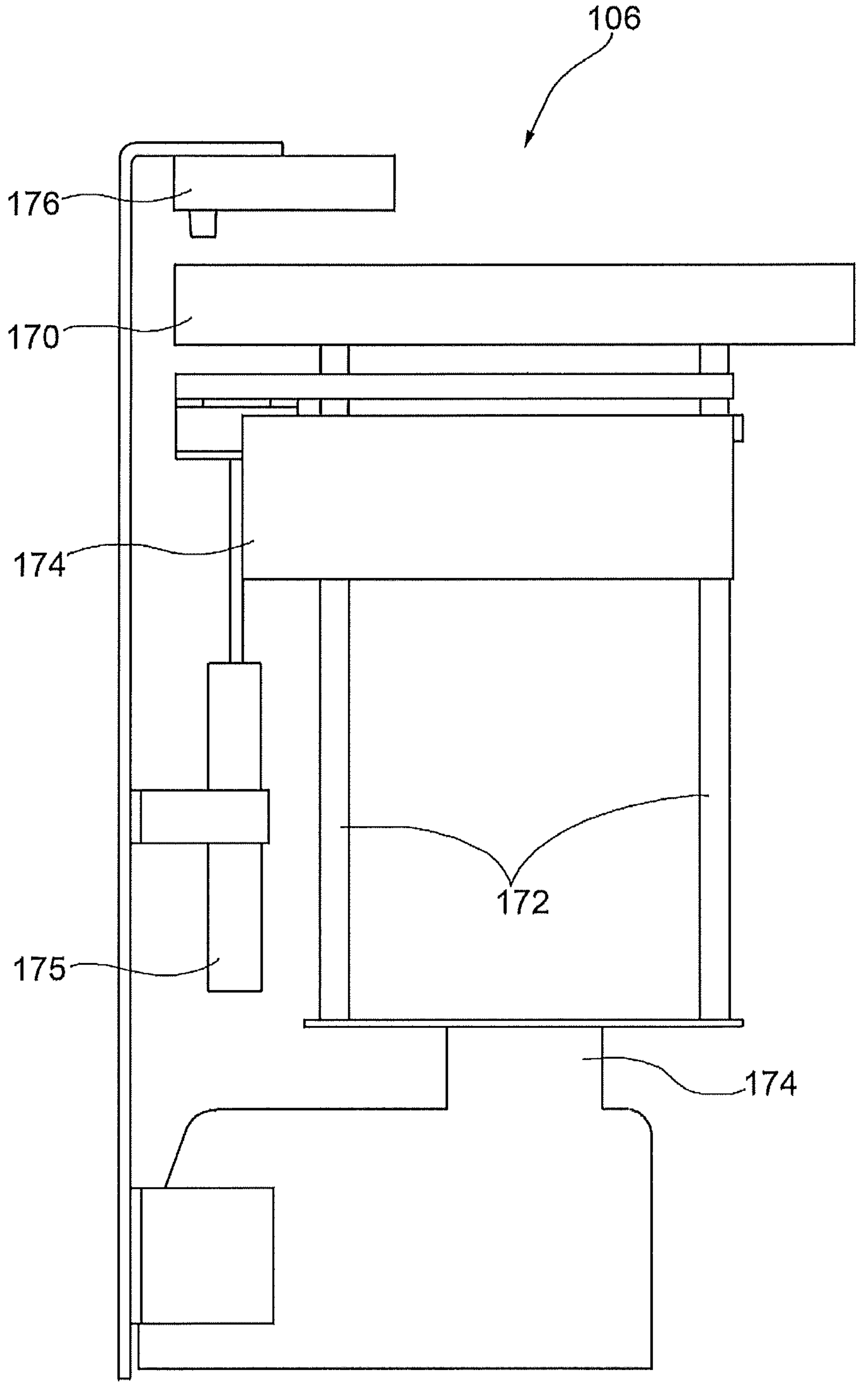
FIG. 23 is an elevation view of the bag weighing group in accordance with the arrow XXIII of FIG. 22.

With reference now to FIGS. 22 and 23, the bag weighing group 106 comprises a bag support 170 which is supported by small arms 172 of a balance 174. There is arranged under the bag support 170 a lifting member 174 which is actuated by a piston 175. The lifting member can press the bag support 170 against an upper projection 176 which acts as an abutment and as a fixed reference. The bag (or other object) which is retained by the bag support 170 can move in translation between two positions. In the first weighing position, the lifting member 174 is lowered and does not interfere with or engage with the bag support 170. In this manner, the bag support 170 is supported only by the arms 172 and therefore completely urges the balance 174. In the weighing position, the bag support 170 is therefore free so that only gravitational force secures it to the balance so as to establish the weight of the object present on the balance apart from a known deviation. In the second stationary position, the lifting member 174 presses the bag support 170 upwards into abutment against the upper projection 176. The movement between the two positions is carried out with a single movement, without any use of a handling robot.

The metering module 100 can also operate autonomously, that is to say, substantially without any need for a robot, for the semi-manual production of the admixtures of medicaments. To that end, the metering module 100 can be, for example, inserted in a laminar flow cabinet and used to automate all the operations which are usually carried out by an operator. In this case, the only task left for the operator is to load the various objects used by the metering module 100, such as syringes, bags, bottles, covers, etc. Once those objects have been loaded, the metering module 100 can carry out the preparation of the medicaments without it being necessary for any other action by the operator. In this manner, there is ensured for the process greater accuracy with respect to manual preparation in a manner similar to what can be carried out with a completely automatic composition by means of the machine which is described above and which is provided with a robot arm.

The metering module 100 has flexible operation which may be adapted to preparations of various types. Consequently, there is described by way of example only one of those processes which can be carried out by means of the metering module 100. A process can, for example, start with loading a syringe S on the metering system. The metering module 100 can then autonomously provide for alignment of the syringe S and the needle in order to provide for the use thereof. For example, it is possible to control the removal of the cover of the needle and/or the insertion of the needle into the syringe S. During the step of arranging the syringe S for use, it is possible to carry out loading of the bottles F' or other objects. The loading process can therefore be carried out at the same time on the same metering module 100. Typically, the bags in which the final product can be injected are loaded on the metering member last, even if this must not be considered to limit the operational and functional possibilities of the metering module 100. During the loading step, that is to say, once the step of loading all the objects has been completely finished, the metering module 100 starts to take the liquids and the medicaments from bags, bottles, ampoules and any other object which might have been loaded. Once the liquid has been drawn in and optionally the weight of the syringe S has been controlled in an automatic manner by means of the syringe weighing group 105, the metering module 100 provides for injecting the liquid into the final recipient container. This final container can in turn be weighed in order to evaluate whether the quantity of liquid injected is correct. The final container may be a bag, a syringe, a bottle or another object which is capable of maintaining a liquid therein.

Finally, the machine, the module and the process of the present invention allow the production of intravenous medicaments with a great rapidity of execution. The typical execution rapidity of a single metering member may be increased in a modular manner with the equipped walls which are provided with the equipment suitable for autonomously carrying out the necessary operations being increased, in an asynchronous manner with respect to the movements of a handling robot used only for the transport of the objects from one position to the other inside the machine.

Naturally, the principle of the invention remaining the same, the forms of embodiment and details of construction may be varied widely with respect to those described and illustrated, without thereby departing from the scope of the present invention.

The invention claimed is:

1. A machine for preparing intravenous medicaments comprising:

an enclosing structure having a plurality of lateral walls defining respective sides of a closed internal working environment;

at least one access station provided on at least one of the lateral walls of the enclosing structure for selective access to the closed internal working environment;

at least one of the lateral walls being a modular equipped wall mounting thereon a plurality of stations grouped together on the modular equipped wall in the closed internal working environment for one or more objects used in preparation of the intravenous medicaments, the plurality of stations comprising:

at least one temporary receiving or parking station configured for temporarily receiving one or more of the objects; and at least one operating station configured for carrying out operations on one or more of the objects;

the modular equipped wall mounting thereon the at least one temporary receiving or parking station and the at least one operating station;

the machine further comprising a handling robot arranged in the closed internal working environment, the handling robot being programmed to transfer the objects from any one of the plurality of stations selected from the at least one access station, the at least one temporary receiving or parking station and the at least one operating station, to any other of the plurality of stations.

2. The machine according to claim 1, wherein the handling robot is arranged in a substantially central position in the closed internal working environment, the handling robot comprising a handling hand and being configured to rotate about a substantially vertical axis so as to be able to reach with the handling hand substantially any position on the lateral walls of the enclosing structure.

3. The machine according to claim 1, wherein the modular equipped wall comprises:

at least one bottle parking station for bottles;

at least one ampoule parking station for ampoules or phials;

at least one syringe parking station for syringes;

at least one bag parking station for bags.

4. The machine according to claim 1, further including a preparation station configured for using intravenous medicaments in a substantially central zone of the modular equipped wall.

5. The machine according to claim 4, further including bottle work supports arranged around the preparation station.

6. The machine according to claim 4, further including a weighing device arranged below the preparation station, the weighing device being configured for weighing a bag and/or a bottle.

7. The machine according to claim 4, wherein the preparation station comprises a syringe support, the syringe support being rotatable about a substantially horizontal axis and movable in a substantially vertical direction, the syringe support including an engaging member for a syringe.

8. The machine according to claim 7, wherein the syringe support comprises a syringe actuator configured for selectively moving a plunger of a syringe gripped by the engaging member in a first direction to operate the syringe in a drawing manner or in a second direction to operate the syringe in an injecting manner.

9. The machine according to claim 1, further including one or more mixers arranged on the modular equipped wall, the one or more mixers being configured for mixing contents of one or more bottles.

10. The machine according to claim 1, wherein the at least one access station is constructed as a transit chamber, the transit chamber being configured so as not to directly expose the closed internal working environment to an environment external to the machine.

11. The machine according to claim 10, wherein the transit chamber has two closure panels or doors, one of the closure panels or doors being directed towards an outer side of the enclosing structure so as to be accessible to an operator in order to introduce or withdraw contents to/from the transit chamber, and the other of the closure panels or doors being directed towards the closed internal working environment of the machine for cooperation with the handling robot.

12. The machine according to claim 1, further including at least one tray for insertion into the at least one access station, the at least one tray being provided with specific receiving members for the objects.

13. The machine according to claim 1, further including at least one tray for insertion into the at least one access station, the at least one tray comprising at least one receiving member comprising a cavity with at least two different internal diameters so as to be able to receive at least two cylindrical objects with different diameters substantially corresponding to the respective different internal diameters of the cavity.

14. The machine according to claim 12, wherein the at least one tray further comprises at least one specific receiving member configured for receiving one or more syringes.

15. The machine according to claim 1, further comprising a system configured for regulating air inside the enclosing structure to maintain environmental conditions ideal for preparing the intravenous medicaments while at the same time preventing discharge of powders or other products dangerous to the health of an operator, or minimizing introduction of contaminants into the enclosing structure.

16. The machine according to claim 15, wherein the system is configured to maintain the closed internal working environment at a negative pressure to prevent discharge of noxious or toxic substances from the enclosing structure.

17. The machine according to claim 15, wherein the system is configured to maintain the closed internal working environment at a positive pressure to prevent introduction of contaminants into the enclosing structure.

18. The machine according to claim 1, further comprising a metering module forming at least one of the lateral walls, the metering module comprising at least one container support group, at least one syringe support/metering member group, and at least one weighing group for weighing objects used in preparation of the intravenous medicaments.

19. The machine according to claim 18, wherein the metering module further comprises at least one needle unscrewing and/or syringe plugging group.

20. The machine according to claim 18, wherein the metering module further comprises at least one washing station.

21. The machine according to claim 18, wherein the metering module comprises one or more baskets for collecting objects allowed to fall by one of the at least one container support group and/or by the at least one syringe support/metering member group.

22. The machine according to claim 18, wherein the at least one weighing group comprises at least one syringe weighing group and/or at least one bag weighing group.

23. The machine according to claim 18, wherein the metering module further comprises a needle unscrewing and/or syringe plugging group, a syringe weighing group, a bag weighing group, a rotating platform and a motor group, the at least one container support group comprises a plurality of container support groups and the at least one syringe support/metering member group comprises a single syringe support/metering member group, the single syringe support/metering member group being arranged in a substantially central position and surrounded radially by the plurality of container support groups, by the needle unscrewing and/or syringe plugging group, by the syringe weighing group and, in a lower position, by the bag weighing group, the single syringe support/metering member group being mounted on the rotating platform, the rotating platform being actuated by the motor group, the motor group allowing the rotating platform to rotate in a vertical plane so as to turn from time to time to the plurality of container support groups, the needle unscrewing and/or syringe plugging group, the syringe weighing group and the bag weighing group.

24. The machine according to claim 18, wherein the at least one container support group comprises a plurality of pairs of pincers arranged to rotate about a substantially horizontal axis.

25. The machine according to claim 18, wherein the at least one syringe support/metering member group comprises a base support rotatable about a first substantially horizontal axis and movable in translation along a second axis transverse to the first axis.

26. The machine according to claim 25, wherein the at least one syringe support/metering member group comprises a pair of pincers for clamping a syringe body, a pair of pincers for clamping a syringe needle and a pair of pincers for clamping a syringe plunger, each of the pair of pincers for clamping the syringe body, the pair of pincers for clamping the syringe needle and the pair of pincers for clamping the syringe plunger being linearly movable.

27. The machine according to claim 19, wherein the at least one needle unscrewing and/or syringe plugging group comprises an operating member having a receiving member for receiving and gripping a syringe cover or a syringe needle, the at least one needle unscrewing and/or syringe plugging group further including a translation member, the operating member being selectively rotatable and being associated with the translation member to press the syringe cover on a syringe or to extract the syringe needle from a syringe.

28. The machine according to claim 18, wherein the at least one weighing group comprises a syringe weighing group with an engaging element, a balance connected to the engaging element, the engaging element being resiliently loaded by a resilient loading action to grip a member to be weighed, a motor member arranged to loosen the engaging element by acting counter to the resilient loading action, the motor member being disengageable from the engaging element to isolate the balance from the motor member so as not to affect ae weight measurement.

29. The machine according to claim 18, wherein the at least one weighing group comprises a bag weighing group with a balance, a bag support connected to the balance and a projecting member, the bag support being selectively liftable into abutment with the projecting member, the projecting member acting as an abutment and as a fixed reference.

30. A process for preparing intravenous medicaments with the machine of claim 1, comprising asynchronous implementation of the following steps:

introduction of objects inside the machine;

removal of objects from the machine;

transfer of objects from a predetermined station to another predetermined station, which is carried out by the handling robot; and subjecting the objects to operations for preparing intravenous medicaments which operations are carried out on the modular equipped wall without the use of the handling robot.

31. The machine according to claim 1, wherein the modular equipped wall is self-contained and includes movement and actuation mechanisms which operate the at least one operating station mounted thereon.

32. The machine according to claim 31, wherein one of the lateral walls other than the modular equipped wall is a non-equipped wall and is not equipped to carry out operations on the objects, the modular equipped wall is a first modular equipped wall, and the machine is configured to permit replacement of the non-equipped wall with a second modular equipped wall.

33. The machine according to claim 32, wherein the second modular equipped wall is identical to the first modular equipped wall.

34. The machine according to claim 31, wherein the modular equipped wall is a first modular equipped wall, and the machine is configured to permit replacement of one of the lateral walls other than the first modular equipped wall with a second modular equipped wall identical to the first modular equipped wall.

* * * * *